United States Patent
Echeverri

(10) Patent No.: US 10,471,427 B2
(45) Date of Patent: Nov. 12, 2019

(54) FLUIDIC MANIFOLD CARTRIDGE SYSTEM

(71) Applicant: Biorep Technologies, Inc., Miami Lakes, FL (US)

(72) Inventor: Felipe Echeverri, Miami Lakes, FL (US)

(73) Assignee: BIOREP TECHNOLOGIES, INC., Miami Lakes, FL (US)

( * ) Notice: Subject to any disclaimer, the term of this patent is extended or adjusted under 35 U.S.C. 154(b) by 271 days.

(21) Appl. No.: 15/494,846

(22) Filed: Apr. 24, 2017

(65) Prior Publication Data

US 2018/0303083 A1    Oct. 25, 2018

(51) Int. Cl.
*B01L 3/00* (2006.01)
*F16K 99/00* (2006.01)
*A01N 1/02* (2006.01)

(52) U.S. Cl.
CPC .... *B01L 3/502738* (2013.01); *F16K 99/0015* (2013.01); *F16K 99/0028* (2013.01); *F16K 99/0059* (2013.01); *B01L 3/502715* (2013.01); *B01L 2200/04* (2013.01); *B01L 2200/0694* (2013.01); *B01L 2300/0887* (2013.01); *B01L 2400/0487* (2013.01); *B01L 2400/0622* (2013.01)

(58) Field of Classification Search
CPC .............. A01N 1/0247; B01L 2200/04; B01L 2200/0694; B01L 2300/0887; B01L 2400/0487; B01L 2400/0622; B01L 3/502715; B01L 3/502738; F16K 99/0015; F16K 99/0028; F16K 99/0059
See application file for complete search history.

(56) References Cited

U.S. PATENT DOCUMENTS

| | | | |
|---|---|---|---|
| 4,650,766 | A | 3/1987 | Harm et al. |
| 4,959,321 | A | 9/1990 | Preece et al. |
| 5,079,160 | A | 1/1992 | Lacy et al. |
| 5,424,209 | A | 6/1995 | Kearney |
| 6,416,718 | B1 | 7/2002 | Maiefski et al. |
| 6,548,263 | B1 | 4/2003 | Kapur et al. |
| 6,653,124 | B1 | 11/2003 | Freeman |

(Continued)

OTHER PUBLICATIONS

Cabrera, et al., "Glutamate is an autocrine signal essential for glucagon release." (21 pages).

(Continued)

*Primary Examiner* — Benjamin R Whatley
(74) *Attorney, Agent, or Firm* — Fox Rothschild LLP

(57) ABSTRACT

A fluidic manifold cartridge includes a plurality of source fluid inlets and fluid outlets. A plurality of fluid input flow channels are provided. Each fluid inlet is in fluid communication with a fluid input flow channel. Each fluid input flow channel directs fluid from the fluid inlet past a plurality of valves. A plurality of fluid output flow channels are in fluid communication with a fluid outlets. Each valve includes a valve seat, a portion of membrane, and a control fluid opening. Each valve has an open and closed condition. The valve in the open condition directs fluid from a fluid input flow channel to a fluid output flow channel. The control fluid opening directs control fluid to move the membrane so as to change the valve between the open and closed conditions. Systems and methods for fluidic manifold are also disclosed.

4 Claims, 64 Drawing Sheets

(56) References Cited

U.S. PATENT DOCUMENTS

| | | | |
|---|---|---|---|
| 6,660,149 B1 | 12/2003 | Karger et al. | |
| 6,833,270 B2 | 12/2004 | Poo et al. | |
| 7,188,994 B2 | 3/2007 | Poo et al. | |
| 7,323,092 B2 | 1/2008 | Karger et al. | |
| 8,263,389 B2 | 9/2012 | Poo et al. | |
| 8,865,427 B2 | 10/2014 | Poo et al. | |
| 2002/0012988 A1 | 1/2002 | Brasile | |
| 2002/0110905 A1 | 8/2002 | Barbera-Guillem et al. | |
| 2003/0069413 A1 | 4/2003 | Pai et al. | |
| 2003/0194332 A1 | 10/2003 | Jahn et al. | |
| 2005/0221269 A1 | 10/2005 | Taylor et al. | |
| 2008/0286746 A1 | 11/2008 | Poo et al. | |
| 2009/0093797 A1 | 4/2009 | Burke et al. | |
| 2011/0020856 A1* | 1/2011 | Poo | C12M 23/12 435/29 |
| 2013/0247691 A1* | 9/2013 | Tokhtuev | B01L 3/50273 73/863.01 |
| 2015/0352549 A1* | 12/2015 | Kolb | F16K 99/0015 422/505 |
| 2016/0195085 A1* | 7/2016 | Van Eemeren | F04B 43/043 417/472 |

OTHER PUBLICATIONS

Cabrera, et al., "Glutamate is a positive autocrine signal for glucagon release," Cell Metabolism (2008) 7: 545: 554.

International Search Report mailed in PCT/IB18/52820 dated Sep. 20, 2018.

* cited by examiner

PERIFUSION MANIFOLD
(FIXED DEAD VOLUME)

8X4 PERIFUSION MANIFOLD
(VARIABLE DEAD VOLUME)

— 474
 TOP ACRYLIC — 360

— 470
 OUTPUT VIA — 350

— 460
 OUTPUT CHANNEL LAYER — 340

— 450
 CHANNEL VIA LAYER — 330

— 440
 INPUT CHANNEL LAYER — 320

— 400
 VALVE LAYERS — 300

○ ○ ○   LAYER 5 (OUTPUT CHANNEL LAYER)

▭▭▭   LAYER 3 (INPUT CHANNEL LAYER)

□ □ □   LAYER 1 (VALVE LAYER)

FLUIDIC MANIFOLD CARTRIDGE SYSTEM

FIELD OF THE INVENTION

The present invention is directed to fluidic manifold systems, and more particularly to fluid flow controls for perifusion systems.

BACKGROUND OF THE INVENTION

Automated perifusion systems offer the advantage of rapid analysis of the impact of various fluids on various samples. In an automated perifusion system, fluids are provided from a plurality of fluid sources and are pumped through a manifold where the fluids, or mixtures of the fluids, are then directed to designated sample containers. The output from the sample containers is collected in identified receptacles so that the user can analyze the collected fluid, and thereby the interaction of the source liquid or mix of liquids on the sample in the respective sample containers. Such systems are described in U.S. Pat. No. 8,865,427 and U.S. Pat. No. 8,263,389, the disclosures of which are herein fully incorporated by reference.

SUMMARY OF THE INVENTION

A cartridge for a fluidic manifold system for directing the flow of source fluids includes a valve layer having a plurality of valve seats, and a plurality of control fluid openings in fluid connection with the valve seats. The valve seats define a fluid flow path from an inlet location to an outlet location. A flexible membrane layer can be proximal and adjacent to the valve layer, and is operable to control fluid flow from the inlet location to the outlet location of the valve seats.

A fluid input channel layer can be adjacent to the flexible membrane layer and on an opposite side of the flexible membrane layer from the valve layer. The fluid input channel layer can include fluid input channels for directing fluid to the inlet locations of the valve seats and can include fluid output openings in communication with the outlet locations of the valve seats;

A fluid via layer can be adjacent the fluid input channel layer. The fluid via layer can include a plurality of fluid output vias in fluid connection with the fluid output openings of the fluid input channel layer, and can include a plurality of fluid input vias in fluid communication with the fluid input channels of the fluid input channel layer.

A fluid output channel layer can be adjacent to the fluid via layer. The fluid output channel layer can include fluid output channels for receiving fluid from the fluid output vias of the fluid via layer, and a plurality of fluid input openings in fluid communication with the fluid input vias of the fluid via layer.

A fluid inlet/outlet layer can be adjacent to the fluid output channel layer. The fluid inlet/outlet layer can include a plurality of fluid inlet openings in fluid communication with the fluid input openings of the fluid output channel layer, and a plurality of fluid outlet openings in fluid communication with the fluid output channels of the fluid output channel layer.

The source fluids can be liquids. The control fluid can be a gas. The fluidic manifold system can be a perifusion system.

A fluidic manifold cartridge for use in directing the flow of source fluids can include a plurality of fluid inlets and fluid outlets, and a plurality of fluid input flow channels. Each fluid inlet can be in fluid communication with a fluid input flow channel. Each fluid input flow channel can direct fluid from the fluid inlet past a plurality of valves. A plurality of fluid output flow channels can be provided. Each fluid outlet can be in fluid communication with a fluid output flow channel. Each valve can include a valve seat, a diaphragm, and a control fluid opening. Each valve can have an open and closed condition. The valve in the open condition can direct fluid from a fluid input flow channel to a fluid output flow channel. The control fluid opening can direct control fluid to move the diaphragm so as to change the valve between the open and closed conditions.

Each fluid input flow channel can be in fluid communication with a plurality of valves. Each fluid output flow channel can be in fluid communication with a plurality of valves. Each valve can uniquely connect one of the fluid input flow channels to one of the fluid output flow channels.

A fluidic manifold cartridge system for directing the flow of source fluids can include a removable fluidic manifold cartridge. The cartridge can include a cartridge housing having a plurality of fluid inlet openings, a plurality of fluid input channels in fluid communication with the fluid inlet openings, a plurality of fluid outlet openings, and a plurality of fluid output channels in fluid communication with the fluid outlet openings. A plurality of control fluid-controlled valves can be in fluid communication with the fluid input channels and the fluid output channels so as to selectively direct flow from the fluid input channels to the fluid output channels. Control fluid conduits extend from openings at an external surface of the cartridge housing to the valves.

A plurality of sample containers can also be provided. The sample containers can have a liquid inlet and a liquid outlet. The sample containers can receive liquid through the inlet and discharge liquid through the outlet. A plurality of liquid sources can be provided for supplying a plurality of liquids to the fluidic manifold cartridge.

The fluidic manifold cartridge can be disposed between the liquid sources and the sample containers. Each fluid source can be in fluid connection to at least one fluidic manifold cartridge fluid inlet opening. Each fluidic manifold cartridge fluid outlet can be in fluid connection with a fluid inlet of a sample container. The plurality of valves selectively directs fluid flow from the fluid sources through the fluidic manifold cartridge fluid output channels. At least one pump can be provided for pumping fluid from the fluid sources to the fluidic manifold cartridge and to respective sample containers.

The fluidic manifold cartridge system can include a fluidic manifold housing. The fluidic manifold housing can include a cartridge holder and a plurality of control fluid ports in fluid communication with the pump. The control fluid ports can be positioned relative to the cartridge holder such that the control fluid ports align with the control fluid conduit openings at the surface of the cartridge when the cartridge is positioned in the cartridge holder. The fluidic manifold housing can include a driver for moving at least one of the control fluid ports and the cartridge relative to one another such that the ports align with and hermetically seal the control fluid conduit openings to fluidly connect the control gas conduits of the cartridge with the ports. At least one control gas pump can be in fluid communication with the control fluid ports.

The fluidic manifold cartridge system can include a receptacle housing having a plurality of receptacles for receiving fluid from the fluid outlets of the sample containers. The plurality of receptacles can be positioned in the receptacle housing such that different receptacles receive samples from different fluid outlets of each of the sample containers. A drive can be connected to the receptacle housing for moving the receptacle housing such that samples from the outlet are collected in the plurality of receptacles. A programmable controller can be provided and can be programmed to operate the driver to move the receptacles at predetermined times, to operate the valves, and to record the position of the valves and the receptacles as a function of time, so as to correlate the fluids that are supplied to each sample container from the plurality of fluid sources with the fluid samples that are received by the receptacles from the sample containers. The cartridge comprises a front face and a back face. The fluid inlet openings and fluid outlet openings can be provided at the front face and the control fluid conduit openings can be provided at the back face. The source fluid can be a liquid. The control fluid can be a gas. The system can be a perifusion system.

A fluidic manifold cartridge can include a cartridge housing including a plurality of fluid inlet openings, a plurality of fluid input channels in fluid communication with the fluid inlet openings, a plurality of fluid outlet openings, and a plurality of fluid output channels in fluid communication with the fluid outlet openings. A plurality of control fluid-controlled valves can be in fluid communication with the fluid input channels and the fluid output channels so as to selectively direct flow from the fluid input channels to the fluid output channel. Control fluid conduits can extend from an external surface of the cartridge housing to the valves.

A method of using a fluidic manifold for directing source fluids can include the step of providing a fluidic manifold cartridge system. The fluidic manifold cartridge system can include a removable fluidic manifold cartridge. The removable fluidic manifold cartridge can include a cartridge housing including a plurality of fluid inlet openings, a plurality of fluid input channels in fluid communication with the fluid inlet openings, a plurality of fluid outlet openings, and a plurality of fluid output channels in fluid communication with the fluid outlet openings. A plurality of control fluid-controlled valves can be in fluid communication with the fluid input channels and the fluid output channels so as to selectively control flow from the fluid input channels to the fluid output channels. Control fluid conduits can extend from openings at an external surface of the cartridge housing to the valves.

A plurality of sample containers can be provided and having a liquid inlet and a liquid outlet. The sample containers receive liquid through the inlet and discharge liquid through the outlet. A plurality of liquid sources are provided for supplying a plurality of liquids to the fluidic manifold cartridge.

The fluidic manifold cartridge can be positioned between the liquid sources and the sample containers, wherein each fluid source is in fluid connection with at least one fluidic manifold cartridge fluid inlet opening, and each fluidic manifold cartridge fluid outlet is in fluid connection with a fluid inlet of a sample container. The operation of the plurality of valves can be controlled to selectively direct fluid flow from the fluid sources through the fluidic manifold cartridge fluid output channels, while operating the at least one pump for pumping fluid from the fluid sources to the fluidic manifold cartridge and to respective sample containers. The method can be used to perform perifusion. The control fluid can be a gas. The source fluid can be a liquid.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

Figure 1:
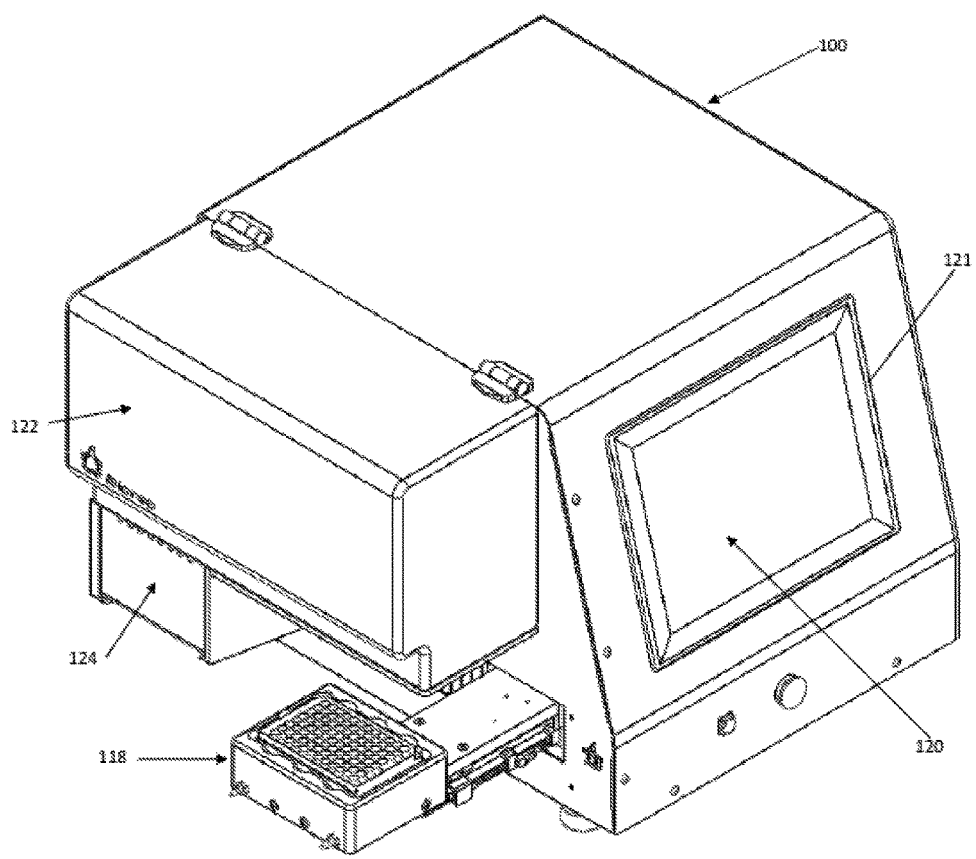
FIG. 1 is a perspective view of a fluidic perifusion system according to the invention.
Figure 2:
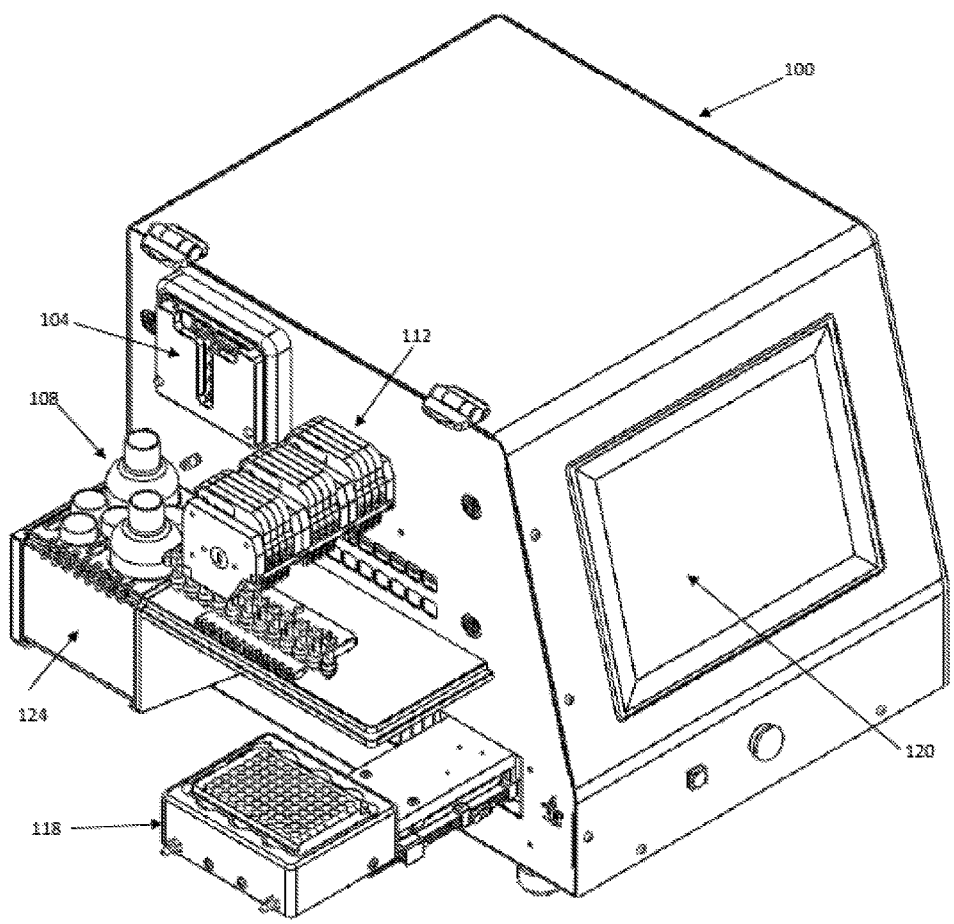
FIG. 2 is a perspective view with a cover removed.
Figure 3:
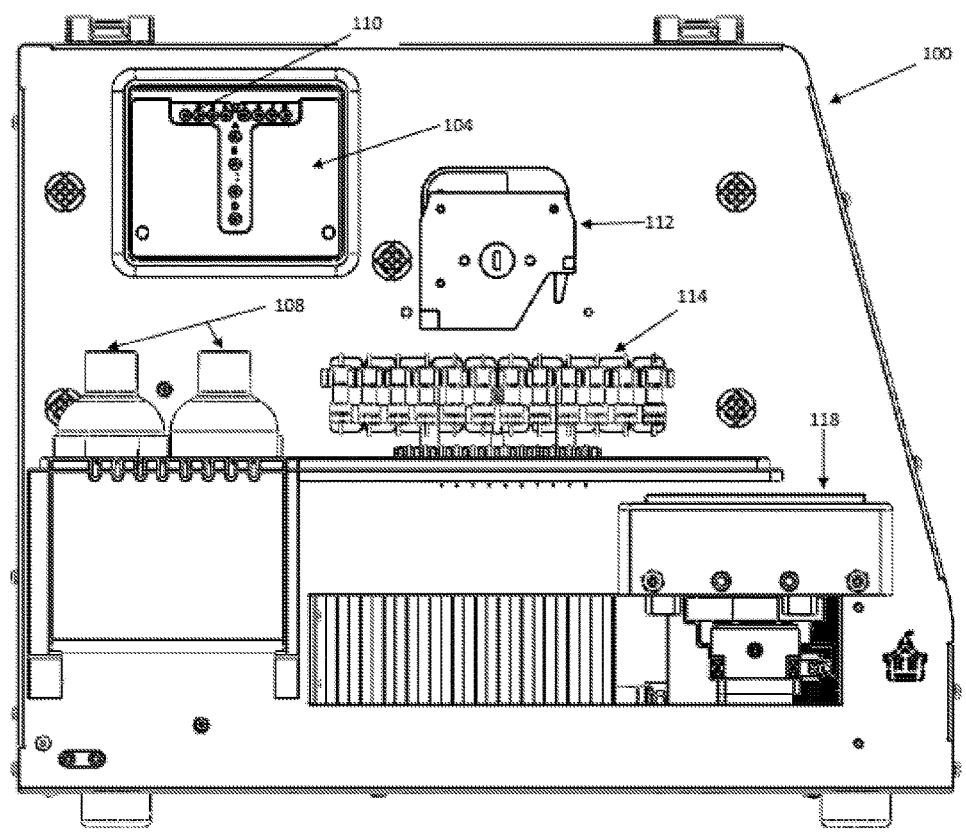
FIG. 3 is a side elevation.
Figure 4:
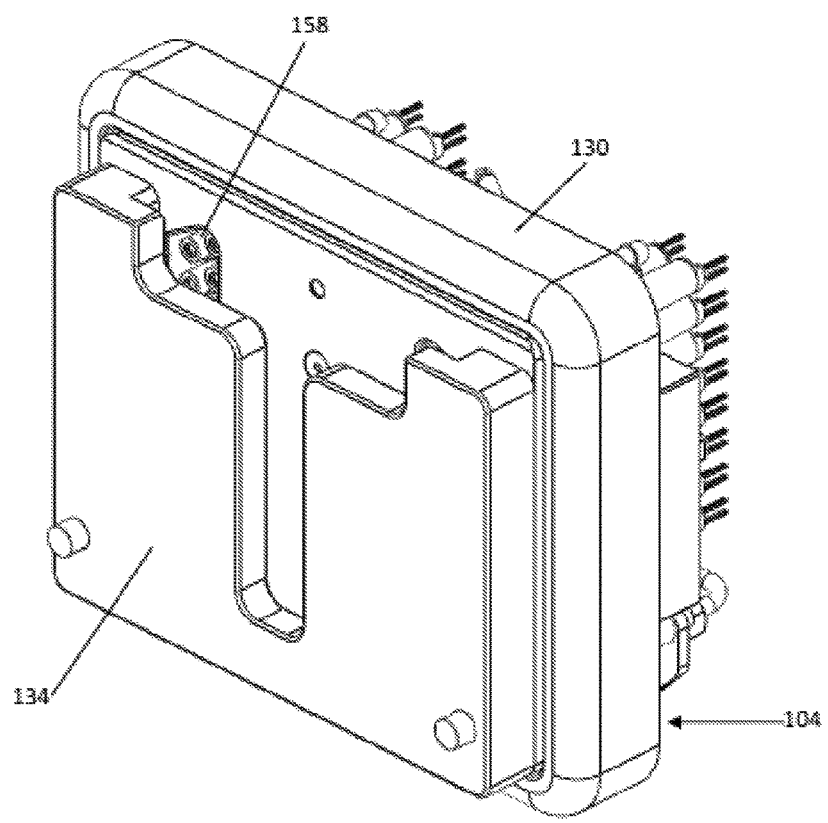
FIG. 4 is a perspective view of a cartridge holder assembly.
Figure 5:
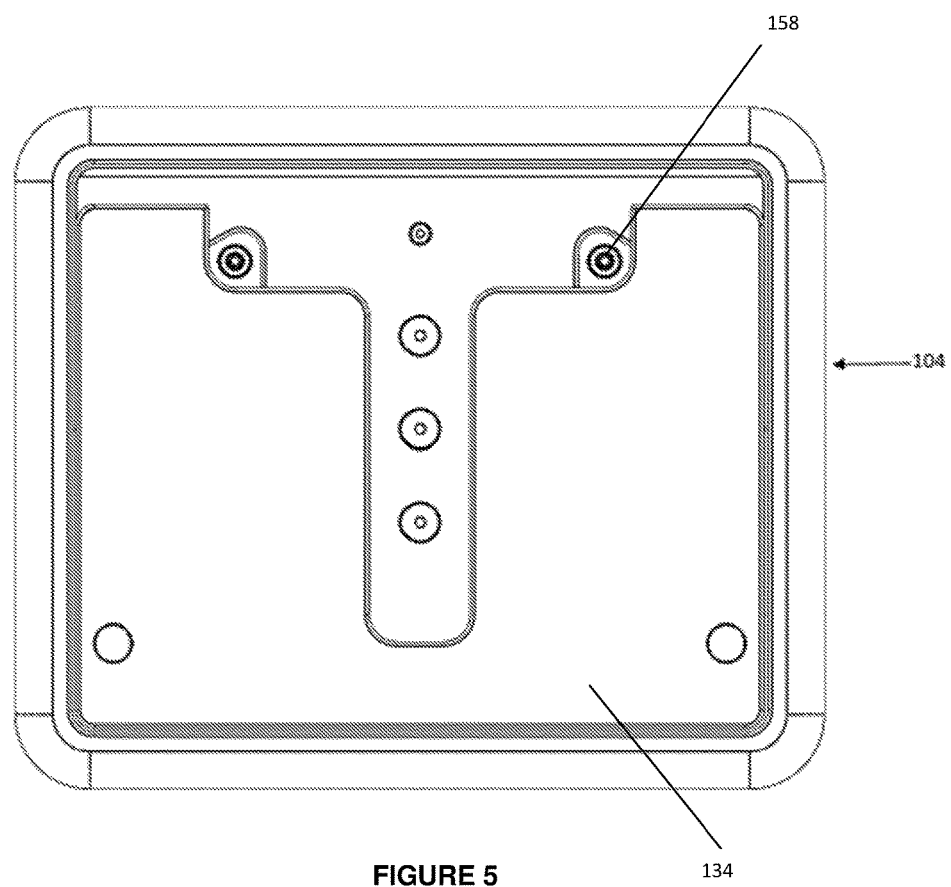
FIG. 5 is a front elevation.

A fluidic manifold cartridge includes a plurality of fluid inlets and fluid outlets. Each fluid inlet is in fluid communication with a fluid input flow channel. The fluid input flow channels direct fluid from the fluid inlet past a plurality of valves. There are a plurality of fluid output flow channels, and each fluid outlet is in fluid communication with a fluid output flow channel.

Each valve has associated therewith a valve seat, a diaphragm, and a control gas or fluid opening. Although the invention will hereafter be described with reference to the control fluid being a control gas, it should be understood that the control fluid can also be a control liquid. The valves have an open and closed condition. The valve in the open condition directs fluid from a fluid input flow channel to a fluid output flow channel. The control gas opening directs control gas to move the diaphragm to change the valve between the open and closed conditions.

Each fluid input flow channel is in fluid communication with a plurality of valves, and each fluid output flow channel is in fluid communication with a plurality of valves. Each valve can uniquely connect one of the fluid input flow channels to one of the fluid output flow channels.

The fluid manifold cartridge can have a layered construction. A valve layer has a plurality of valve seats, and a plurality of control gas openings in fluid connection with the valve seats, such that the valve seats define a fluid flow path from an inlet location to an outlet location. A flexible diaphragm layer can be proximal and adjacent to the valve layer, and operable to control fluid flow from the inlet location to the outlet location of the valve seats. A fluid input channel layer can be adjacent to the flexible diaphragm layer, and on an opposite side of the flexible diaphragm layer from the valve layer. The fluid input channel layer can include fluid input channels for directing fluid to the inlet locations of the valve seats and fluid output openings in communication with the outlet locations of the valve seats. A fluid via layer can be adjacent to the fluid input channel layer. The fluid via layer includes a plurality of fluid output vias in fluid connection with the fluid output openings of the fluid input channel layer, and can include a plurality of fluid input vias in fluid communication with the fluid input channels of the fluid input channel layer. A fluid output channel layer can be adjacent to the fluid via layer, and can include fluid output channels for receiving fluid from the fluid output vias of the fluid via layer, and a plurality of fluid input openings in fluid communication with the fluid input vias of the fluid via layer. A fluid inlet/outlet layer can be adjacent to the fluid output channel layer, and can include a plurality of fluid inlet openings in fluid communication with the fluid input openings of the fluid output channel layer, and a plurality of fluid outlet openings in fluid communication with the fluid output channels of the fluid output channel layer.

A fluidic manifold cartridge system can include a removable and replaceable fluidic manifold cartridge. The cartridge has a housing including a plurality of fluid inlet openings, a plurality of fluid input channels in fluid communication with the fluid inlet openings, a plurality of fluid outlet openings, and a plurality of fluid output channels in fluid communication with the fluid outlet openings.

A plurality of gas-controlled valves are in fluid communication with the fluid input channels and the fluid output channels so as to selectively control flow from the fluid input channels to the fluid output channels. Control gas conduits extend from openings at an external surface of the cartridge housing to the valves.

A plurality of sample containers can be provided. The sample containers have a liquid inlet and a liquid outlet, and the sample containers receive liquid through the liquid inlet and discharge liquid through the liquid outlet. A plurality of liquid sources can be provided for supplying a plurality of liquids to the fluidic manifold cartridge.

The fluidic manifold cartridge is disposed between the liquid sources and the sample containers. Each fluid source is in fluid connection to at least one fluidic manifold cartridge fluid inlet opening. Each fluidic manifold cartridge fluid outlet is in fluid connection with a fluid inlet of a sample container. The plurality of valves are operable to control fluid flow from the fluid sources through the fluidic manifold cartridge fluid output channels. One or more pumps can be provided for pumping fluid from the fluid sources to the fluidic manifold cartridge and to respective sample containers.

A fluidic manifold housing can have a cartridge holder and a plurality of control gas ports in fluid communication with a control gas source. The control gas can provide positive or negative pressure. The control gas ports are positioned relative to the cartridge holder such that the control gas ports align with the control gas conduit openings at the surface of the cartridge when the cartridge is positioned in the cartridge holder.

The fluidic manifold housing can also have a driver for moving at least one of the control gas ports and the cartridge relative to one another such that the ports align with and hermetically seal the control gas conduit openings to fluidly connect the control gas conduits of the cartridge with the control gas ports.

A receptacle housing can have a plurality of receptacles for receiving fluid from the fluid outlets of the sample containers. The plurality of receptacles can be positioned in the receptacle housing such that different receptacles receive samples from different fluid outlets of each of the sample containers. A drive can be connected to the receptacle housing for moving the receptacle housing such that samples from the outlet are collected in the plurality of receptacles.

A programmable controller can be provided to control one or more operations of the fluidic manifold system. The controller can be programmed to operate the driver to move the receptacles at predetermined times, to operate the valves and the pumps, and to record the position of the valves and the receptacles as a function of time so as to correlate the fluids that are supplied to each sample container from the plurality of fluid sources with the fluid samples that are received by the receptacles from the sample containers.

The cartridge can include a front face and a back face, and the fluid inlet openings and fluid outlet openings can be provided at the front face and the control gas conduit openings are provided at the back face. Other orientations are possible.

A method of performing a fluidic manifold function can include the step of providing a fluid fluidic manifold cartridge system, where the fluid fluidic manifold cartridge system includes a removable fluidic manifold cartridge. The cartridge has a cartridge housing with a plurality of fluid inlet openings, a plurality of fluid input channels in fluid communication with the fluid inlet openings, a plurality of fluid outlet openings, and a plurality of fluid output channels in fluid communication with the fluid outlet openings. A plurality of gas-controlled valves are in fluid communication with the fluid input channels and the fluid output channels so as to selectively control flow from the fluid input channels to the fluid output channels. Control gas conduits extend from openings at an external surface of the cartridge housing to the valves. Sample containers are provided having a liquid inlet and a liquid outlet, and the sample containers receiving liquid through the inlet and discharging liquid through the outlet. A plurality of liquid sources supplies a plurality of liquids to the fluidic manifold cartridge. The fluidic manifold system can operate with fluids that can be liquids, gases, or mixtures thereof.

The fluidic manifold cartridge is positioned between the liquid sources and the sample containers, wherein each fluid source is in fluid connection with at least one fluidic manifold cartridge fluid inlet opening, and each fluidic manifold cartridge fluid outlet is in fluid connection with a fluid inlet of a sample container.

The operation of the plurality of valves is controlled to control fluid flow from the fluid sources through the fluidic manifold cartridge fluid output channels, while operating the at least one pump which can include multiple channels for pumping fluid from the fluid sources to the fluidic manifold cartridge and to respective sample containers.

There is shown in FIGS. 1-17 a fluidic manifold cartridge manifold system according to the invention. The system 100 includes a fluidic manifold cartridge holder assembly 104, fluidic manifold fluid sources 108, a fluidic manifold cartridge 110, and one or more fluidic manifold pumps 112 to drive liquid through sample containers 114 and to a collection receptacle 118 (FIGS. 1-4). The system is operated through a programmable controller or computer 120 or other suitable control device, and can have a suitable graphical user interface 121. The cartridge holder assembly 104, fluidic manifold cartridge 110 and fluidic manifold pumps 112 can be contained within a suitable cover 122. The fluidic manifold fluid sources 108 can be stored in a suitable compartment 124.

Figure 20:
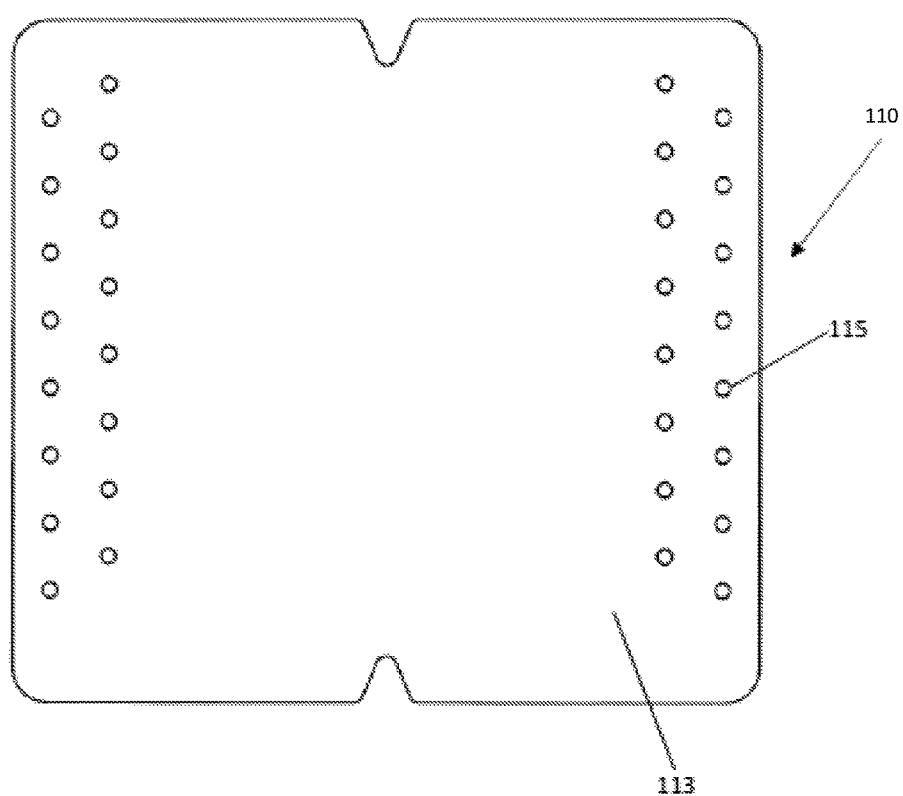
FIG. 20 is a rear elevation.
Figures 21, 22:
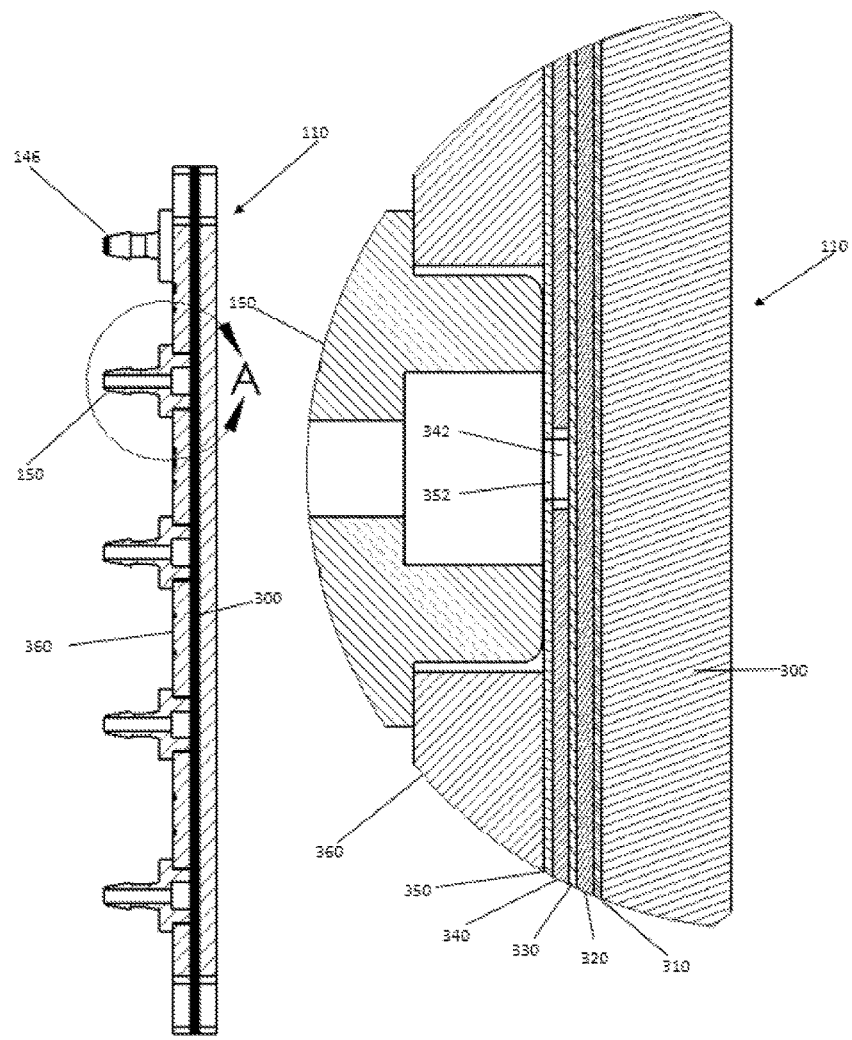
FIG. 21 is a cross section taken along line A-A in FIG. 18.
FIG. 22 is an expanded view of detail A in FIG. 21.
Figure 23:
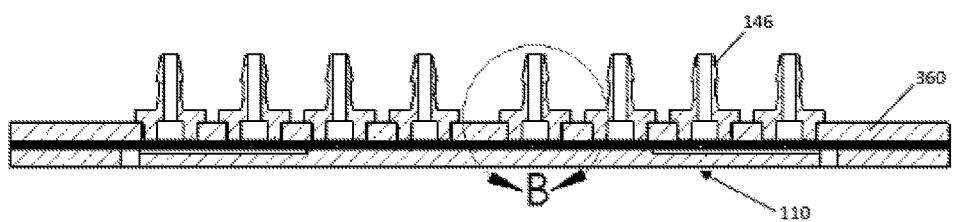
FIG. 23 is a cross-section taken along line B-B in FIG. 18.
Figure 24:
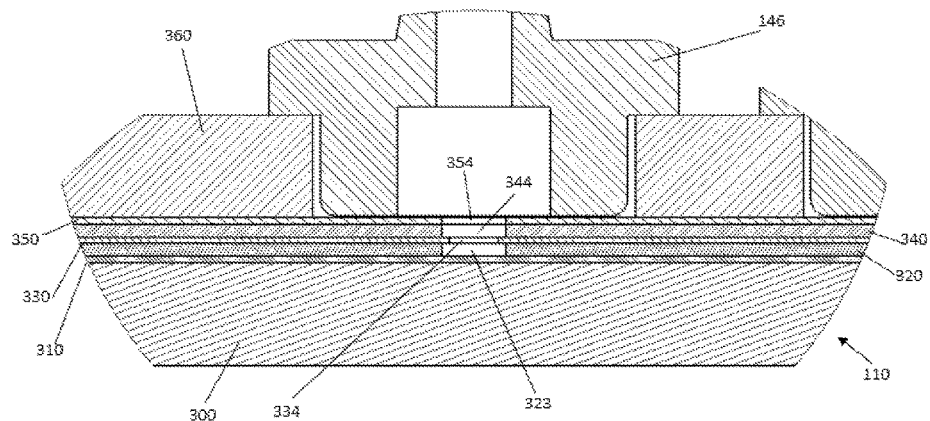
FIG. 24 is an expanded view of detail B in FIG. 23.
Figures 25, 26:
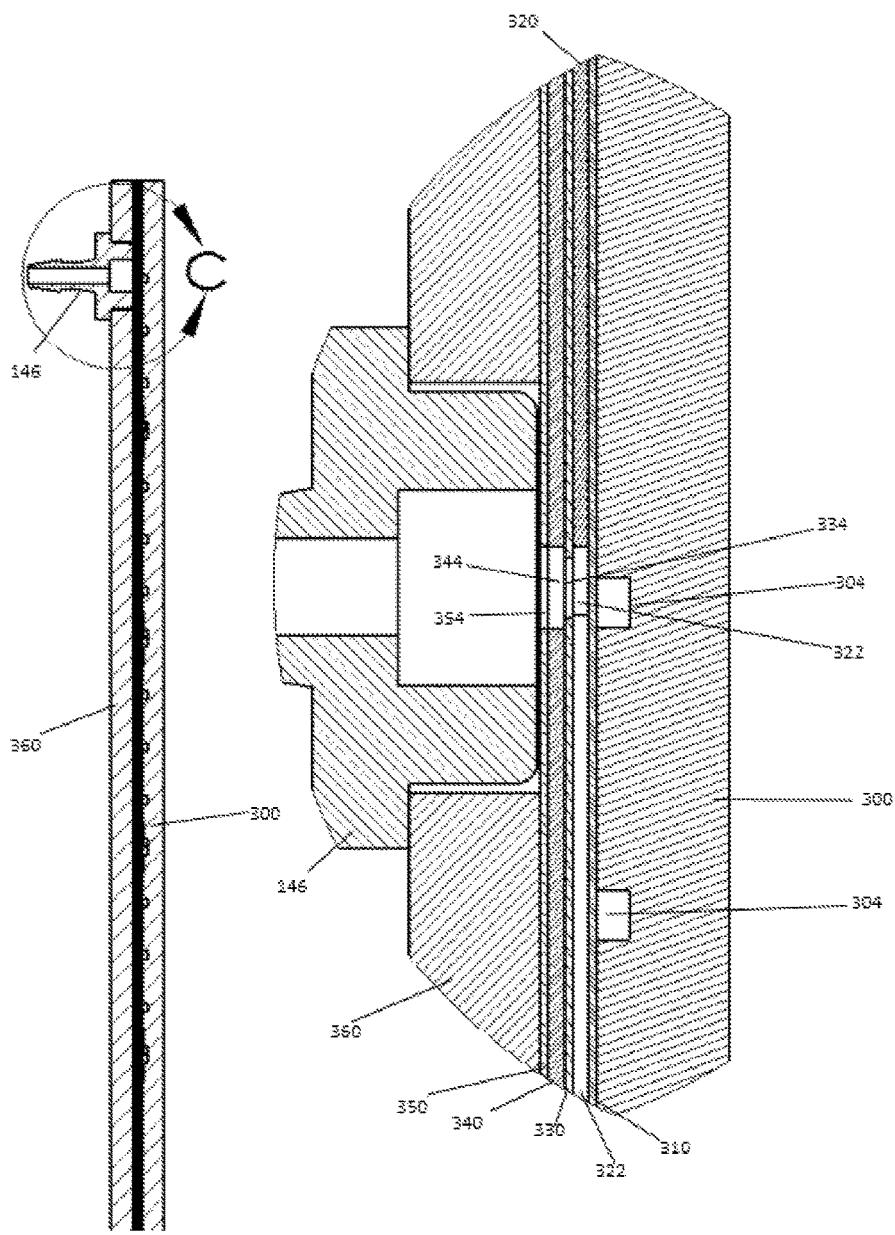
FIG. 25 is a cross-section taken along line C-C in FIG. 18.
FIG. 26 is an expanded view of detail C in FIG. 25.
Figure 27:
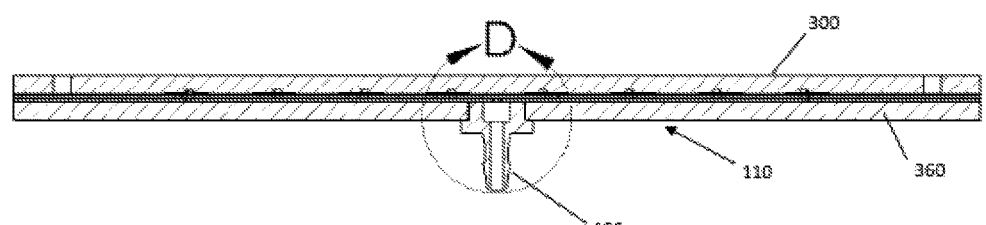
FIG. 27 is cross-section taken along line D-D in FIG. 18.
Figure 28:
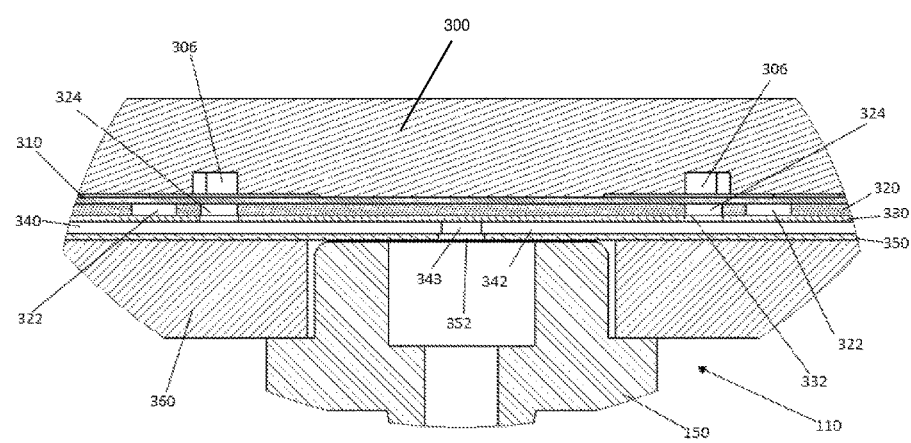
FIG. 28 is an expanded view of detail D in FIG. 27.
Figure 29:
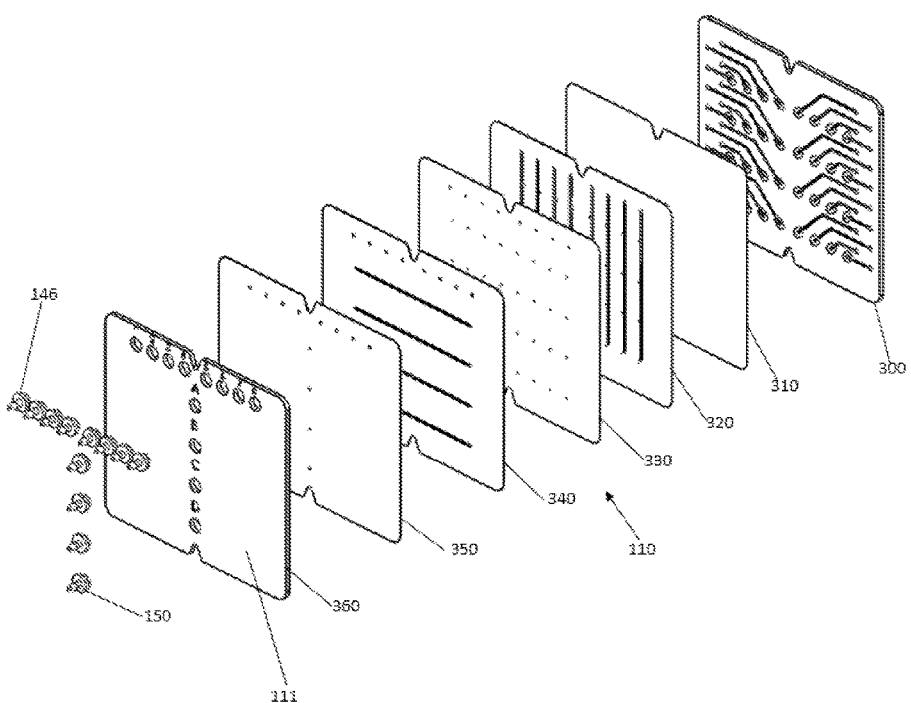
FIG. 29 is an exploded perspective of a fluidic manifold cartridge.

The cartridge 110 has suitable fluid inlets such as inlet ports 146 and suitable fluid outlets such as outlet ports 150 in a front face 111 of the cartridge 110. Other positioning of the fluid inlets and outlets is possible. The cartridge 110 also comprises a plurality of suitable control gas openings 115 in a rear face 113 of the cartridge 110 (FIG. 20). The system 100 utilizes the control gas to operate the valves within the fluidic manifold cartridge 110 according to programming to direct fluid from the sources 108 through the fluid inlet ports 146 to the appropriate outlet ports 150. Appropriate conduits such as tubing (not shown) connects the outlet ports 150 to the appropriate pumps 112 and sample containers 114.

Figure 6:
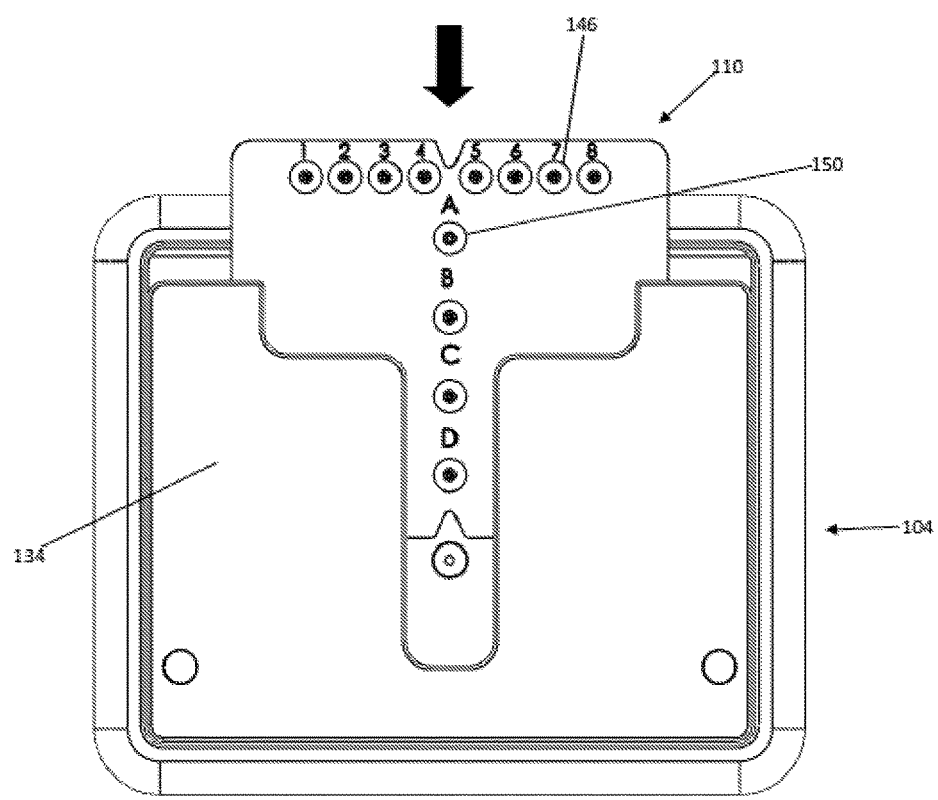
FIG. 6 is a front elevation illustrating the insertion of a fluidic manifold cartridge.
Figure 7:
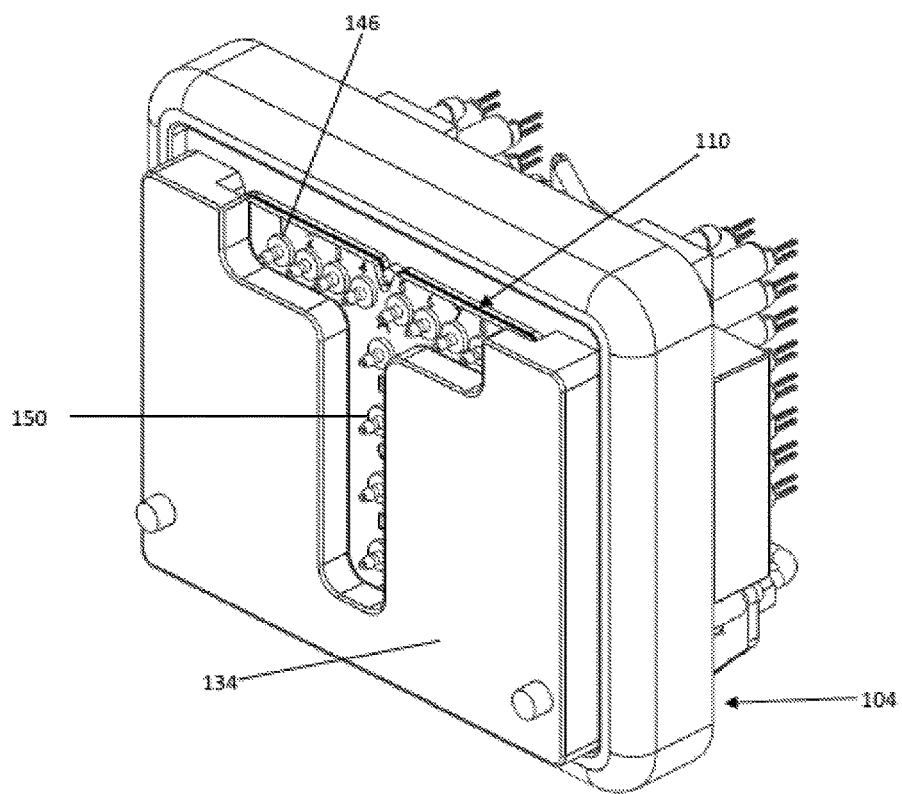
FIG. 7 is a perspective view of a cartridge holder assembly with a cartridge inserted into the cartridge holder assembly.
Figure 8:
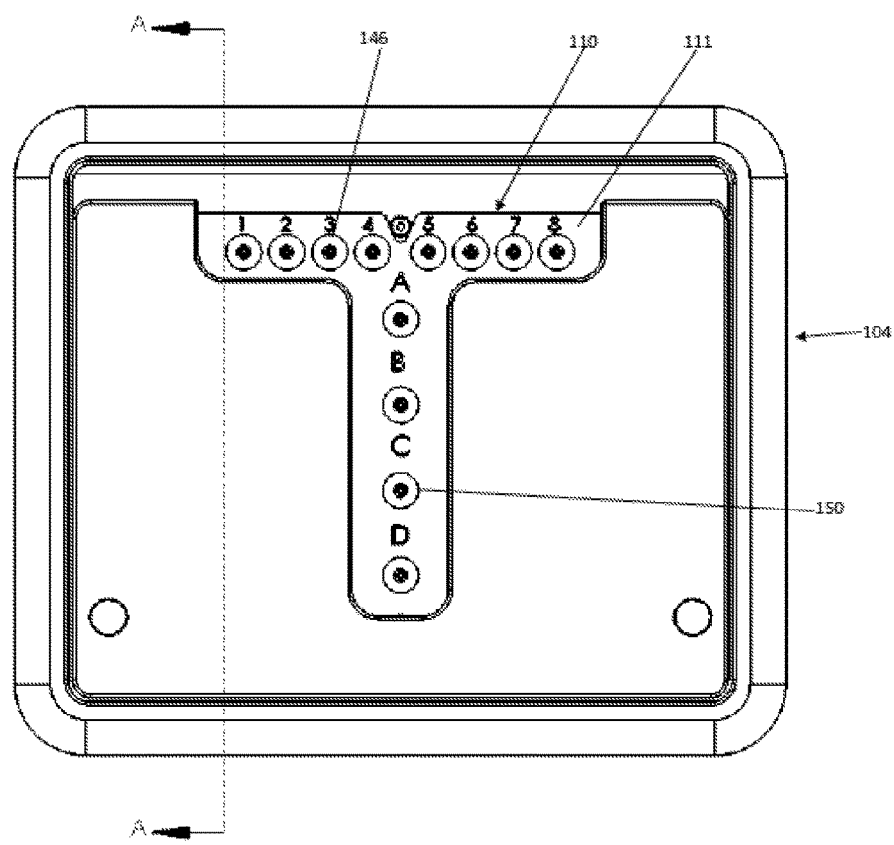
FIG. 8 is a front elevation.
Figure 9:
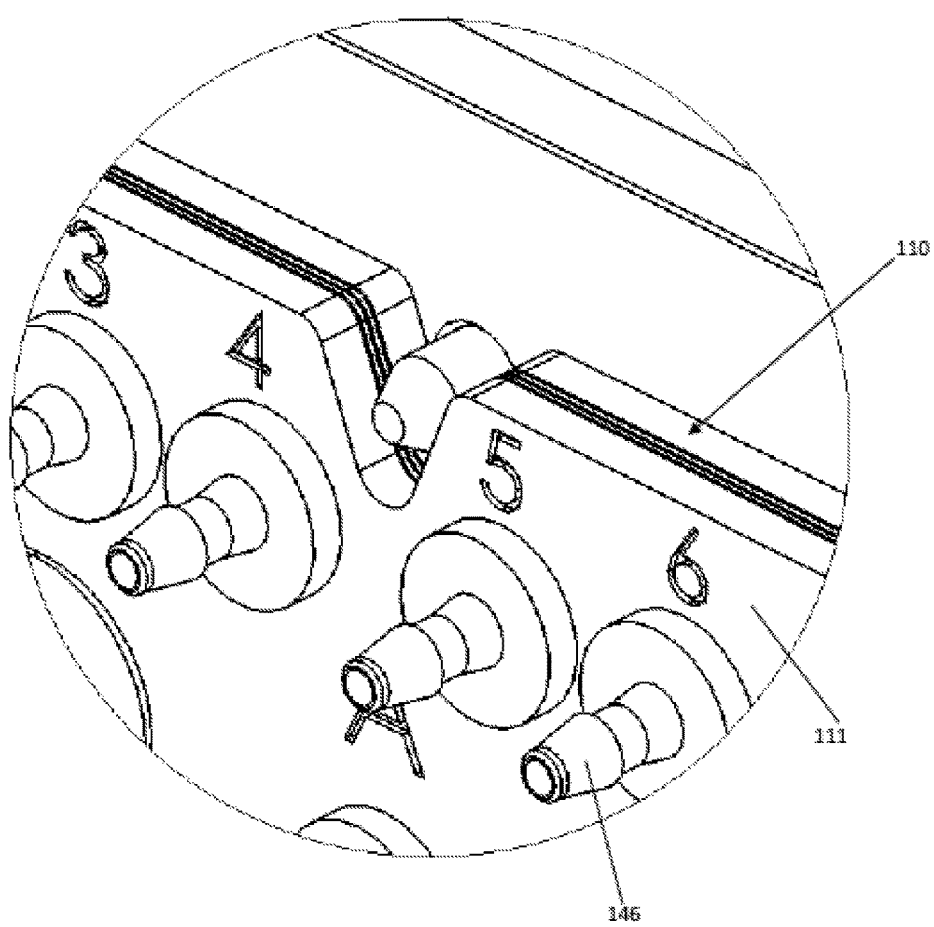
FIG. 9 is an expanded perspective view of a fluidic manifold cartridge in a fluidic manifold cartridge assembly.

The cartridge holder assembly 104 includes a control gas manifold 130 and a clamp 134 that is spaced apart from the control gas manifold 130 to provide a slot for the insertion of the fluidic manifold cartridge 110. The cartridge 110 is positioned in the space between the clamp 134 and control gas manifold 130 (FIGS. 6-7). The control gas manifold 130 has a plurality of control gas fittings or gaskets 158 (FIG. 5) that align with the control gas openings 115 at the back face 113 of the cartridge 110.

Figure 12:
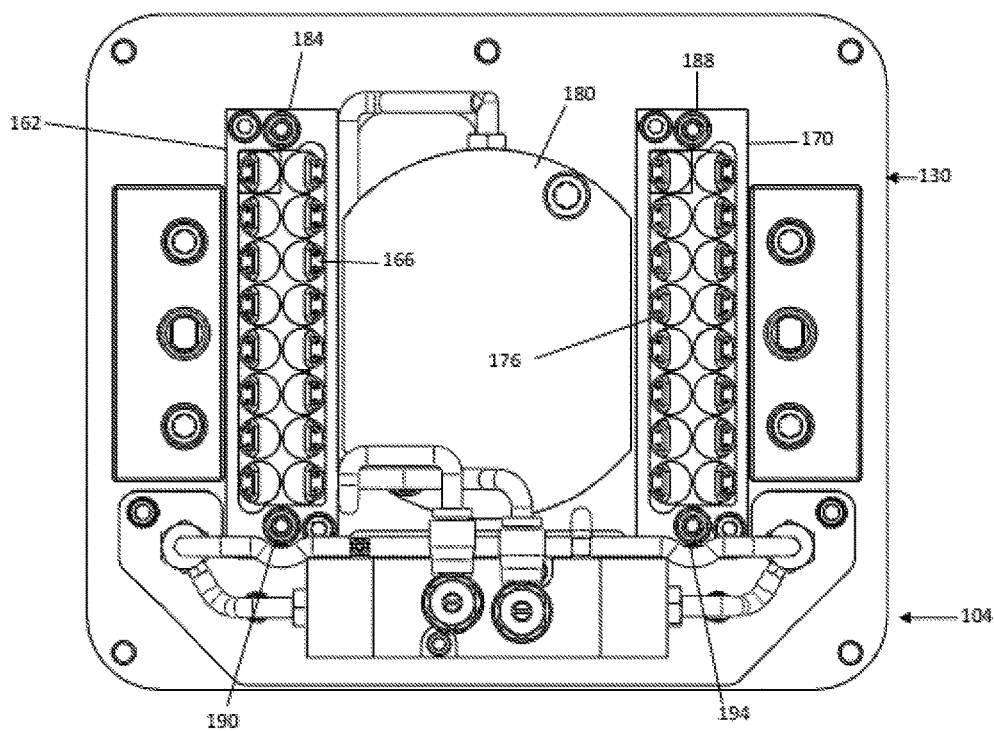
FIG. 12 is a rear elevation of a fluidic manifold cartridge holder assembly.

The clamp 134 and control gas manifold 130 are then brought together to secure the fluidic manifold cartridge 110 in position with the control gas gaskets 158 sealed around the control gas openings 115 of the fluidic manifold cartridge 110 when the fluidic manifold cartridge is positioned between the control gas manifold 130 and the clamp 134. Control gas can thereby be selectively delivered to the fluidic manifold cartridge 110 to selectively operate the valves within the fluidic manifold cartridge 110. The clamp 134 can be moved relative to the control gas manifold 130 to clamp the cartridge 110 in position by any suitable mechanical, electrical or pneumatic driver 180 that is located at the rear of the control gas manifold 130 (FIG. 12). In one embodiment, the clamp 134 is connected to a solenoid or pressurized actuator 180 that moves the clamp 134 according to control signals of the controller or processor 120. The clamp 134 can have a horizontal slot or opening 138 to permit access to the inlet ports 146 and a vertical slot or opening 142 to permit access to the output ports 150. Fluid connection tubes can thereby be secured from the fluid sources 108 to the cartridge 110.

Figure 10:
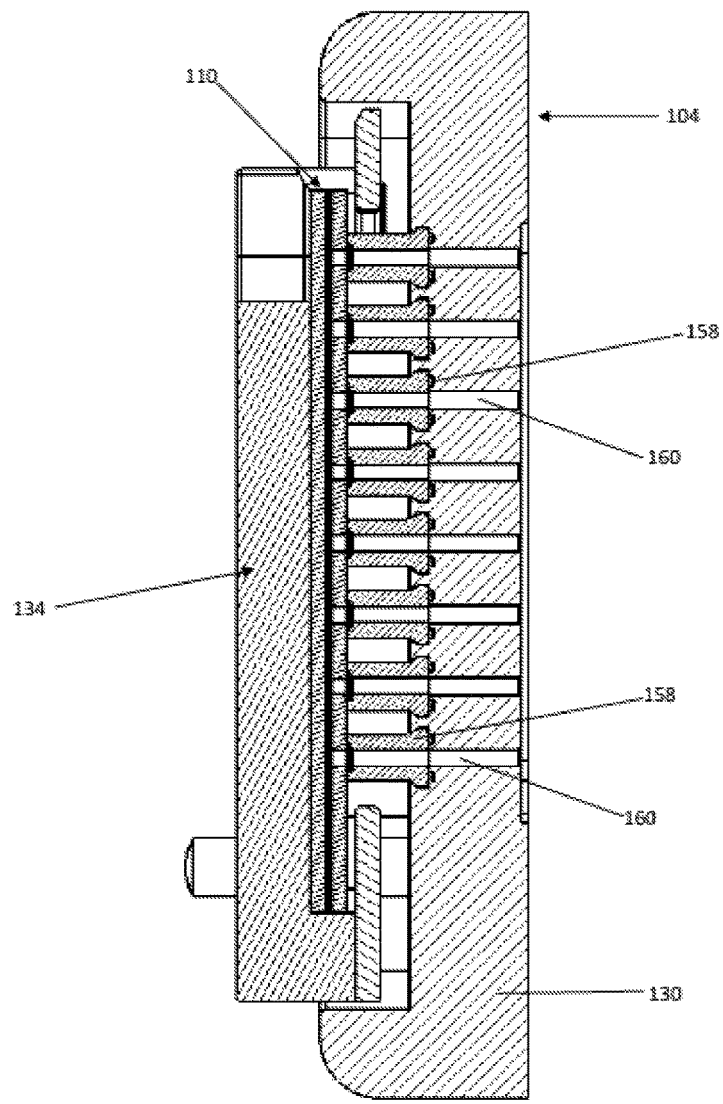
FIG. 10 is a cross-section taken along line A-A in FIG. 8.
Figure 11:
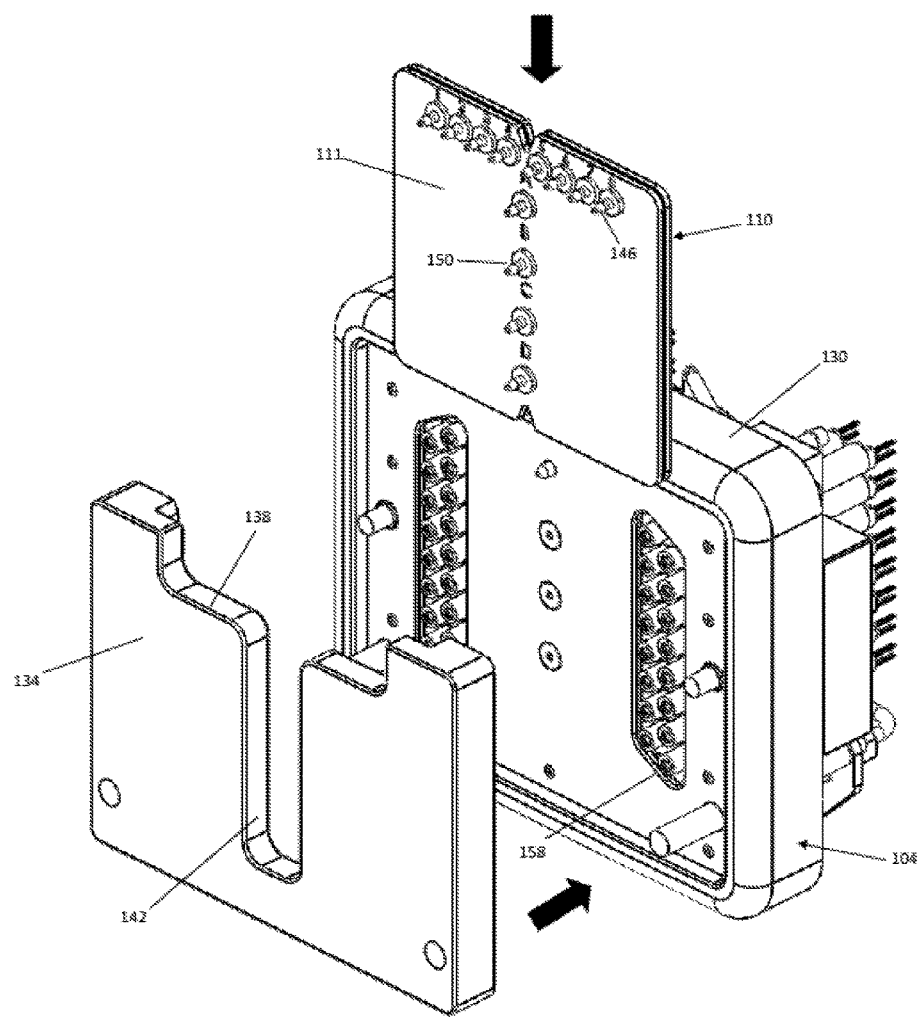
FIG. 11 is an exploded perspective of a cartridge holder assembly with a cartridge.

The gaskets 158 communicate with control gas conduits 160 of the control gas manifold 130 (FIG. 10). The control gas conduits 160 communicate with control gas valves at the rear of the control gas manifold 130 (FIG. 12). Many different control systems for the control gas are possible. In the embodiment shown, the system has a first valve module 162 and a second valve module 170 for controlling the flow of control gas to the control gas conduits 160 and thereby to the control gas openings 115 of the cartridge 110. The first valve module 162 has a plurality of controllable gas valves 166, and the second valve module 170 has a second plurality of controllable gas valves 176. The controllable gas valves 166 and 176 individually control gas flow to each of the control gas conduits 160 and thereby to the control gas openings 115 of the fluidic manifold cartridge 110. The controllable gas valves 166 and 176 can have any suitable construction, and in one embodiment are solenoid-activated and connected to a suitable programmable controller such as the controller 120 to control the operation of the valves.

The control gas for controlling the operation of the valves within the fluidic manifold cartridge 110 can be positive pressure or negative pressure (vacuum). In one embodiment, the control gas is both positive pressure and negative pressure to control the position of a flexible valve membrane within the fluidic manifold cartridge 110. The controllable gas valves 166 and 176 operate to connect the control gas openings 115 to positive or negative pressure sources according to the commands of the programmable controller. The first valve module 162 can have a positive pressure input 184 and a negative pressure (vacuum) input 190. The second valve module 170 can have a positive pressure input 188 and a negative pressure (vacuum) input 194. The controllable gas valves 166 and 176 are independently connected to the positive and negative pressure sources within the first valve module 162 and second valve module 170, such that upon command from the programmable controller 120 each of the valves can individually supply positive or negative pressure to the respective control gas opening 115.

Figure 13:
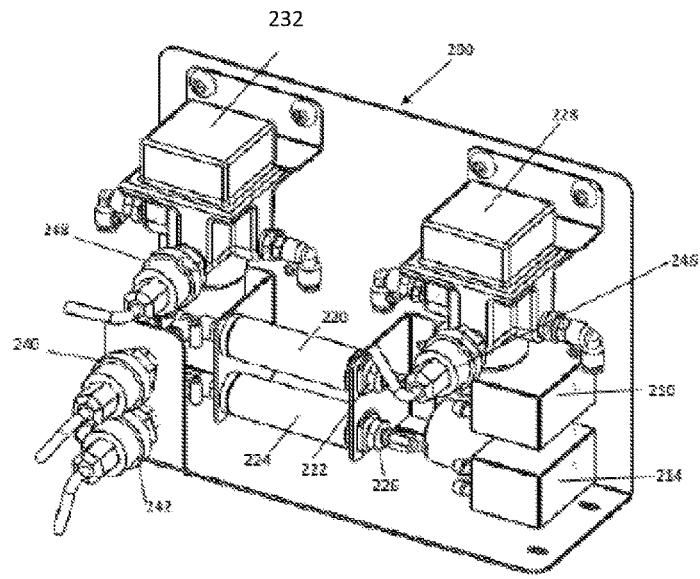
FIG. 13 is a perspective view of a control fluid supply assembly.
Figure 14:
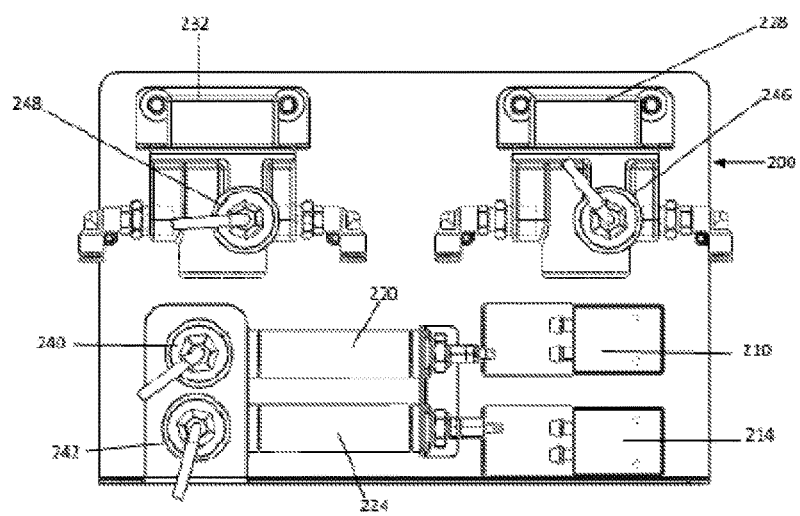
FIG. 14 is a rear elevation.
Figure 15:
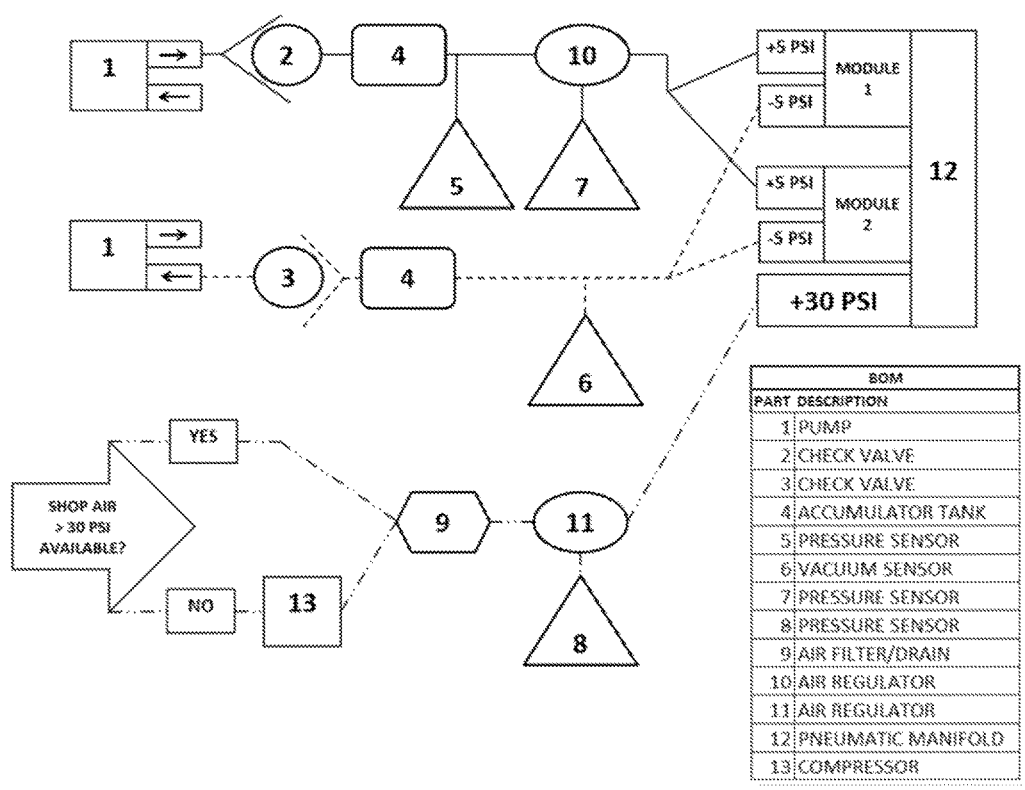
FIG. 15 is a fluid circuit diagram.

A control gas supply assembly 200 is shown in FIGS. 13-14. The system 200 can include a positive pressure pump 210 and a negative pressure (vacuum) pump 214. Alternatively, the pumps could be replaced by connections to external positive and negative pressure sources. The positive pressure pump 210 can be connected to a positive pressure accumulator 220 with a fitting 222. The negative pressure pump 214 can be connected to a negative pressure accumulator to 224 with a fitting 226. A positive pressure sensor 240 can be provided to sense positive pressure and provide a signal to the programmable controller 120. A negative pressure sensor 242 can be provided to sense negative pressure (vacuum) and provide a signal to the programmable controller 120. A low-pressure regulator 228 (for example, 5 psi) and a high-pressure regulator 232 (for example 60 psi) can be provided. The low-pressure regulator 228 provides control gas pressure regulation to the first valve module 162 and second valve module 170 through the positive pressure inputs 184 and 188. A low-pressure regulator sensor 246 can sense pressure at the low-pressure regulator 228 and a high pressure sensor 248 can sense the pressure at the high pressure regulator 232. The sensors also provide a signal to the programmable controller 120. A pneumatic circuit diagram for the system is shown in FIG. 15.

Figure 16:
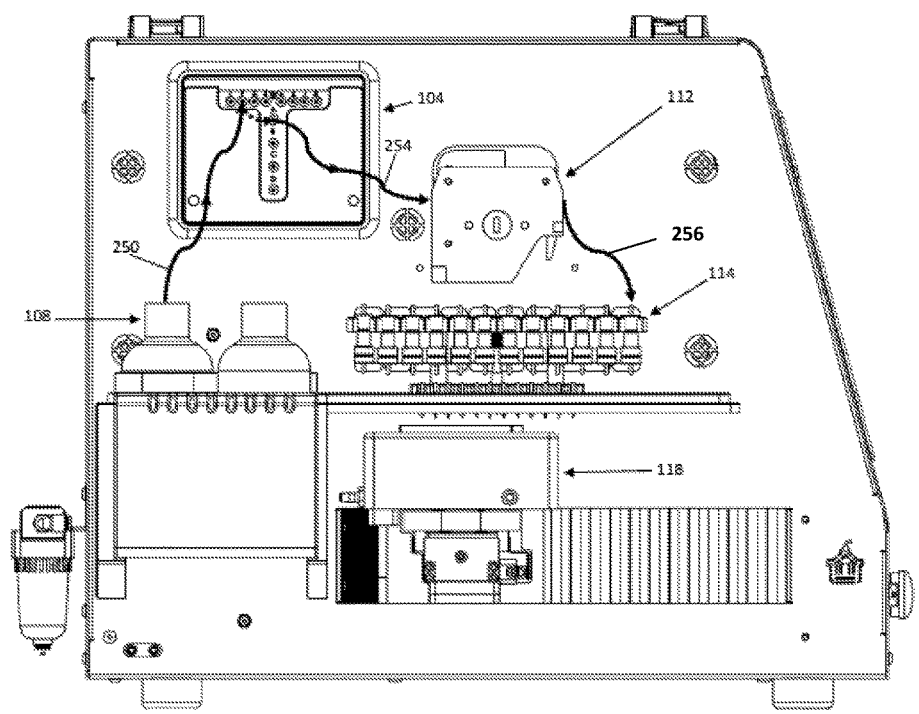
FIG. 16 is a schematic side elevation of a fluidic manifold system illustrating fluidic manifold fluid flow in a first mode of operation.
Figure 17:
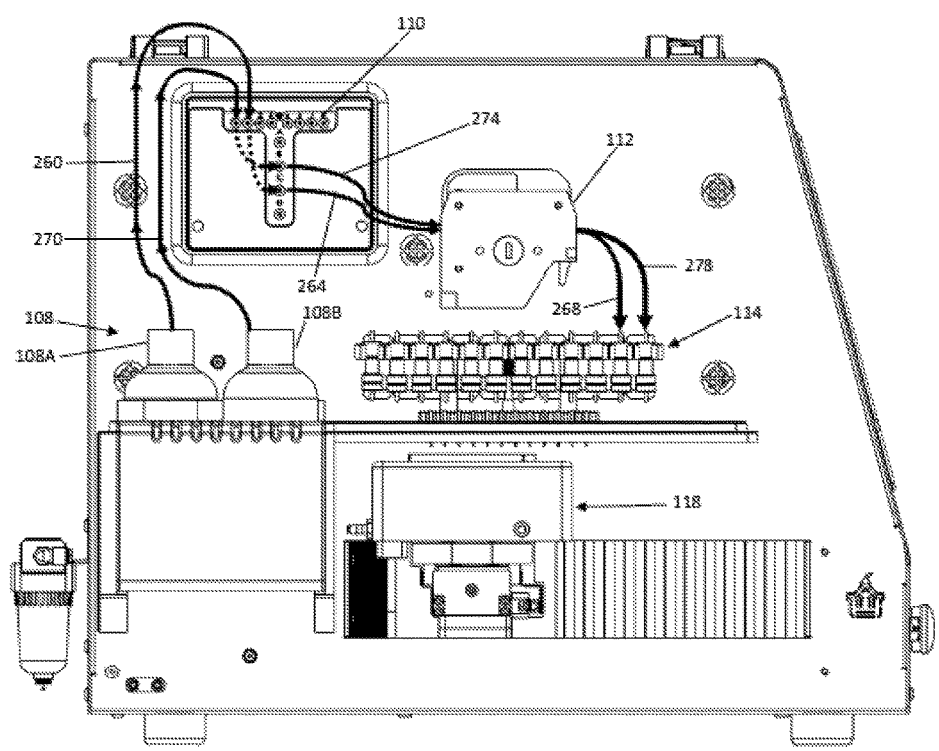
FIG. 17 is a schematic side elevation of a fluidic manifold system illustrating fluidic manifold fluid flow and a second mode of operation.
Figure 18:
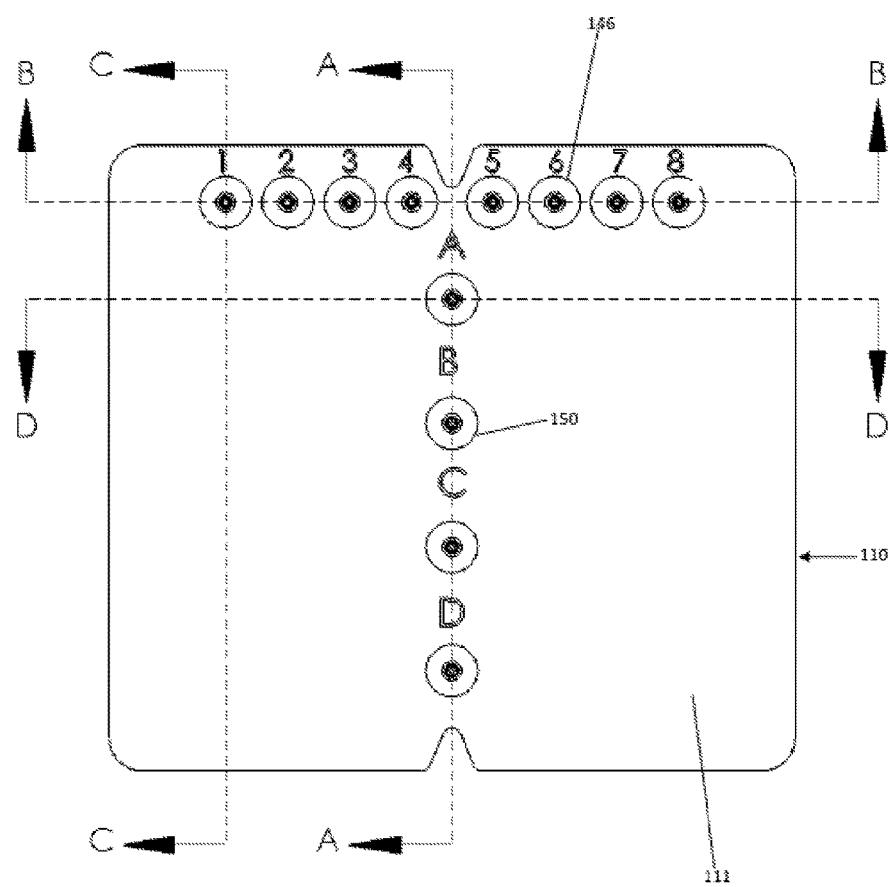
FIG. 18 is a plan view of a fluidic manifold cartridge.
Figure 19:
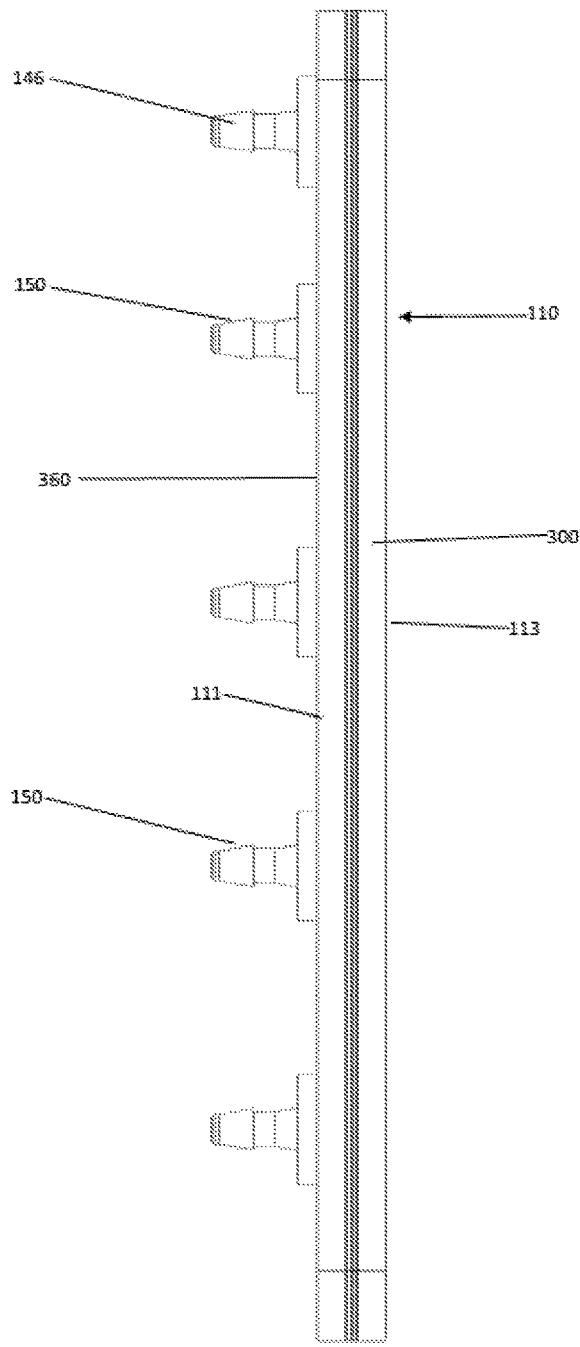
FIG. 19 is a side elevation.

The fluidic manifold process of the system 100 is shown schematically in FIG. 16 where fluid from the source 108 is directed through conduit 250 to the cartridge 110 and is directed through the cartridge 110 by operation of the system to the output conduit 254. The pumps 112 operate to move the liquid through the conduit 256 to the sample containers 114. Sample liquid leaving the sample containers 114 is then collected in the receptacles 118. The simultaneous control of multiple fluid sources is depicted in FIG. 17. In this example, there are two fluid sources 108A and 108B being utilized. Fluid leaves source 108A through a conduit 260 and fluid leaves source 108B through a conduit 270. The fluid is directed through the cartridge 110 by suitable control of the valves within the cartridge 110, which is directed by the programmable controller 120 acting on the controllable gas valves 166 and 176. This will direct the fluid from the source 108A through an output conduit 264, and through the pumps 112 and a sample conduit 268 to a particular sample container 114. Fluid from the source 108B leaves the cartridge 110 through an appropriate output conduit 274 and travels to pump assembly 112 and through a sample conduit 278 particular sample container 114. Each sample can be collected by the collection receptacle 118 in a particular well or subdivision thereof. The controller 120 tracks and records the well and the time where and when a given sample from a given fluid source 108 and a given sample container 114 has been collected. The system is operable to simultaneously control and track the flow of many different fluid sources 108 through many different samples in the sample containers 114.

The system is also capable of mixing fluids from one or more fluid sources 108 and directing these to a sample container 114. It is possible to open and close valves at different duty cycles to create "mixtures" and therefore the possibility of creating a linear gradient. For example, using a low glucose solution (for example 3 mM) and a high glucose solution (for example 20 mM), it is possible to create outputs which, in the case of stimulating cells in the sample containers 114, stimulate the cells with a linear, more physiological glucose concentration varying linearly from 3 mM to 20 mM. It is also possible to control 3 or more valves to achieve additional combinations (such as also varying the concentration of a drug in addition to the linear glucose gradient).

Control periods varying from 1 second to 10 seconds have been tested with good success. Higher control periods can result in mixing not being achieved properly leading to an oscillating stimulation. An example of a linear gradient from 3 mM to 20 mM in Z seconds can be illustrated as follows.

Assumptions:
Control Period (CP) of 1 second
Input 1=low glucose=3 mM (could also be water)
Input 2=high glucose=20 mM
Output A=mixed solution
Cycle 1 (occurring at Time=0)
Valve A1=open for 1.00 second
Valve A2=open for 0.00 seconds
Cycle 2 (occurring 1 second after Cycle 1)
Valve A1=open for 0.99 seconds
Valve A2=open for 0.01 seconds
Cycle 3 (occurring 1 second after Cycle 2)
Valve A1=open for 0.98 seconds
Valve A2=open for 0.02 seconds
This process continues to step:
Cycle X (occurring 1 second after Cycle X-1)
Valve A1=open for 0.02 seconds
Valve A2=open for 0.98 seconds Cycle W (occurring 1 second after Cycle X)
Valve A1=open for 0.01 seconds
Valve A2=open for 0.99 seconds
Cycle Z (occurring 1 second after Cycle W)
Valve A1=open for 0.00 seconds
Valve A2=open for 1.00 second It is important to consider the amount of time it takes to open the valve once energized as well as to close the valve once de-energized. In addition, it is important to consider the amount of time it takes for the pressure to build up and apply full force pushing the membrane in the microfluidic cartridge. Finally, it is important to consider the time it takes for the valve membrane in the microfluidic cartridge to move one way or the other with pressure or vacuum. All these factors influences the control period and the ability of the valves to cycle fast enough (in the order or milliseconds).

An embodiment of the cartridge 110 is shown in FIGS. 18-38. Many different designs of the cartridge 110 are possible. The cartridge 110 can be constructed by any suitable method. The cartridge 110 shown in FIGS. 18-38 is formed of a layered construction, however, other methods such as additive manufacturing or molding can be utilized to form an integral cartridge construction. Although the embodiment shown in FIGS. 18-38 has a particular number of layers and arrangement a number of through holes (vias), fluid channels, control gas openings and channels, and valves and valve constructions, it will be appreciated that many alternatives to the precise arrangements shown are possible.

Figure 30:
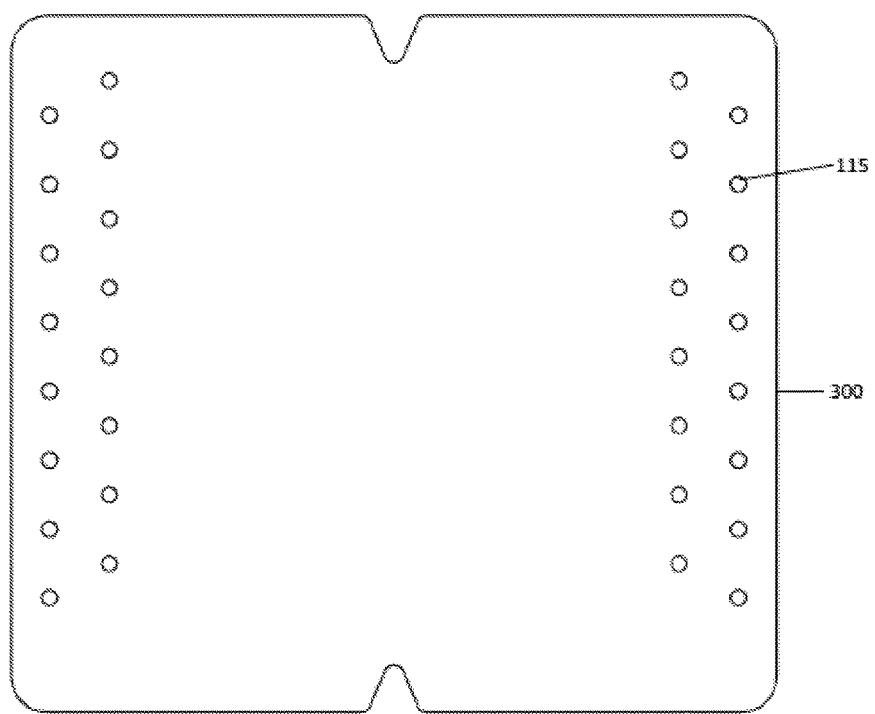
FIG. 30 is a rear elevation of a valve layer of the fluidic manifold cartridge.
Figure 31:
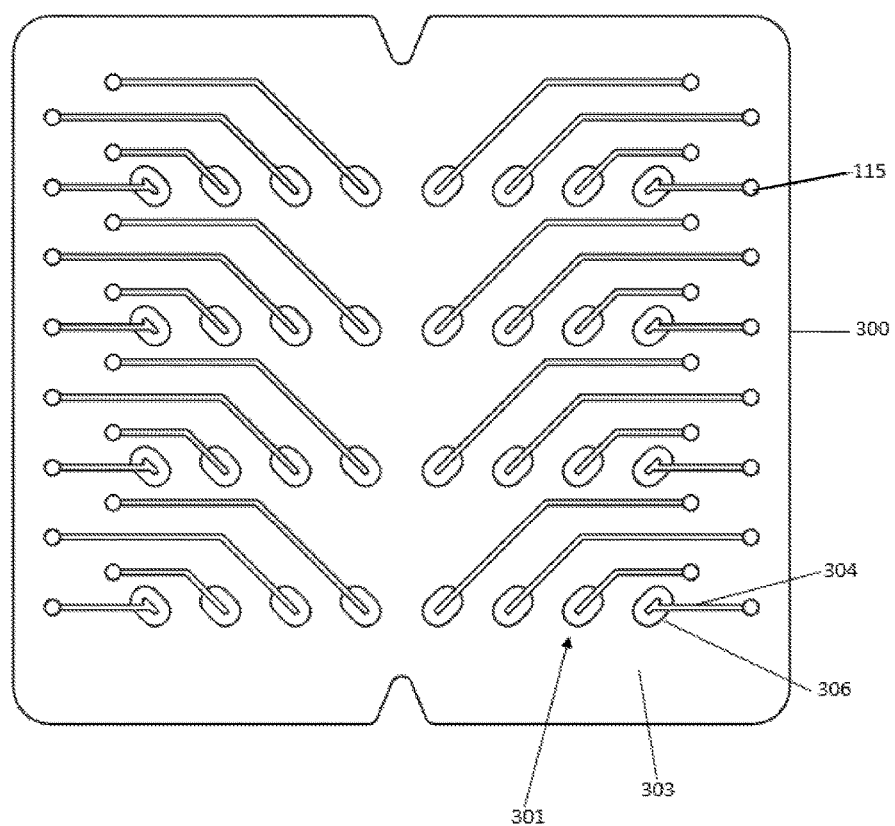
FIG. 31 is a front elevation of the valve layer.
Figure 32:
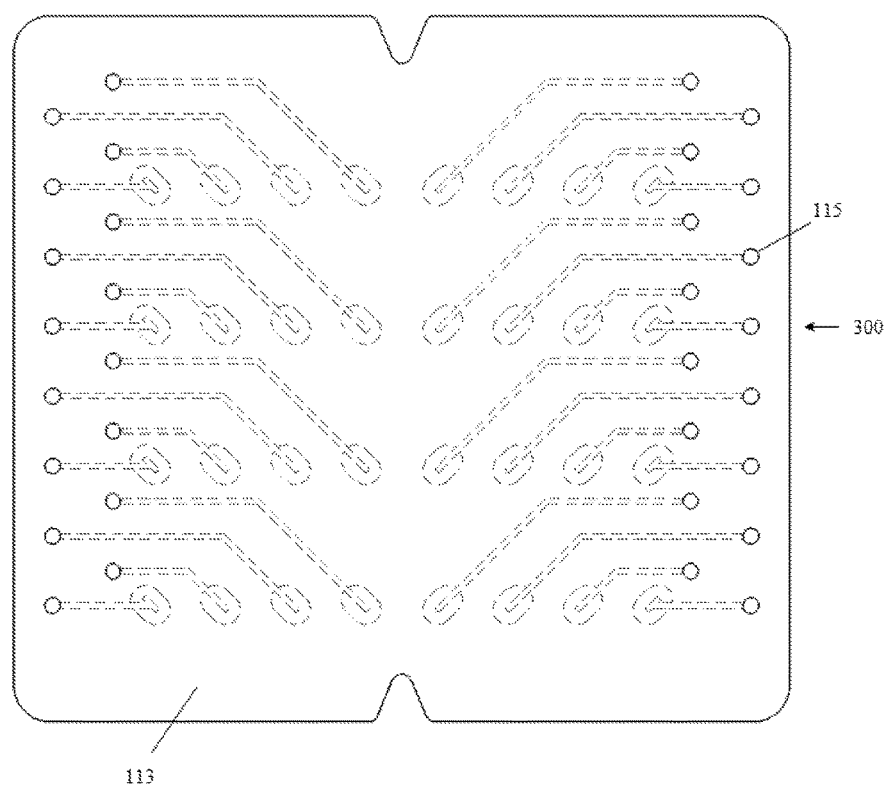
FIG. 32 is a rear elevation illustrating fluid flow path and valves in phantom.
Figure 41:
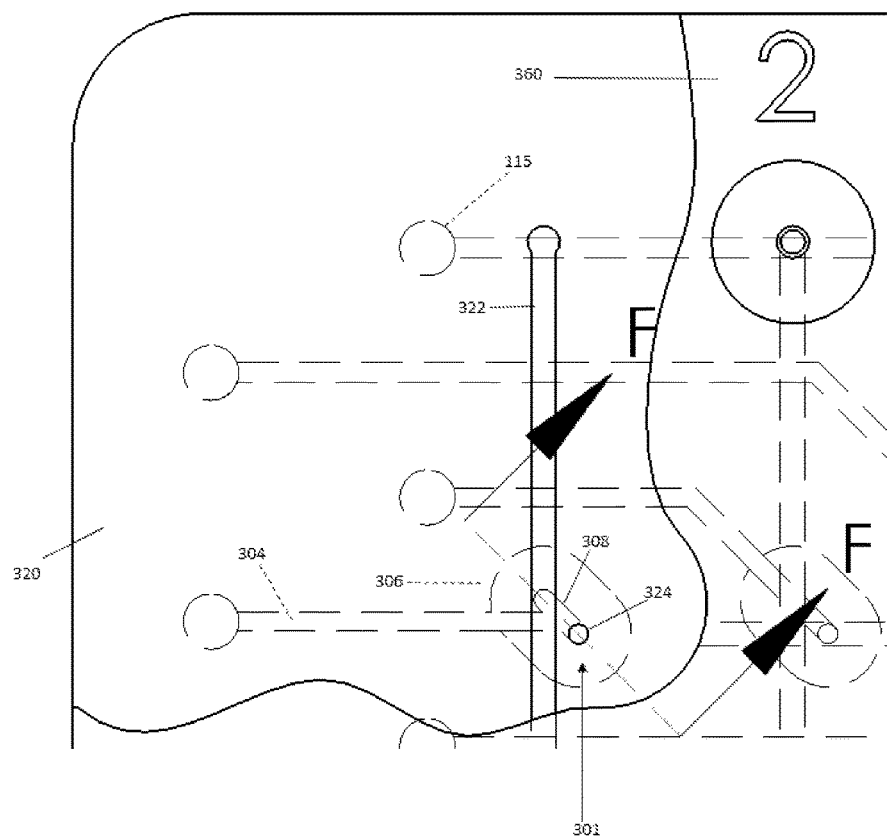
FIG. 41 is a plan view partially broken away and partially in phantom of a portion of a fluidic manifold cartridge with control fluid conduit and valves shown in phantom.

There is shown in FIGS. 30-32 a valve layer 300. This layer of the cartridge 110 abuts the control gas manifold 130 when the cartridge 110 is engaged to the cartridge holder assembly 104. A back face 113 of the valve layer 300 has a plurality of the control gas openings 115 which receive control gas flow through the gaskets 158 and control gas conduits 160 of the control gas manifold 130. The control gas openings 115 extend through the valve layer 300. Each control gas opening 115 communicates with a control gas channel 304 and an associated valve 301 with a valve seat 306 that are formed in a front face 303 of the valve layer 300. The control gas channels 304 fluidly communicate with valve seats 306. This can be seen by the phantom lines in FIG. 32. The valve seats 306 are depressions in the front face 303 of the valve layer 300, and allow a flexible valve membrane to move into the valve seat 306 upon the application of negative pressure (vacuum) from the control gas manifold 130 through the control gas openings 115 and control gas channels 304. This will open the valve 301 to fluid flow. The valve seats 306 further include flow depressions or valve channels 308 (FIGS. 41-42) to direct fluid flowing through the valve.

Figure 33:
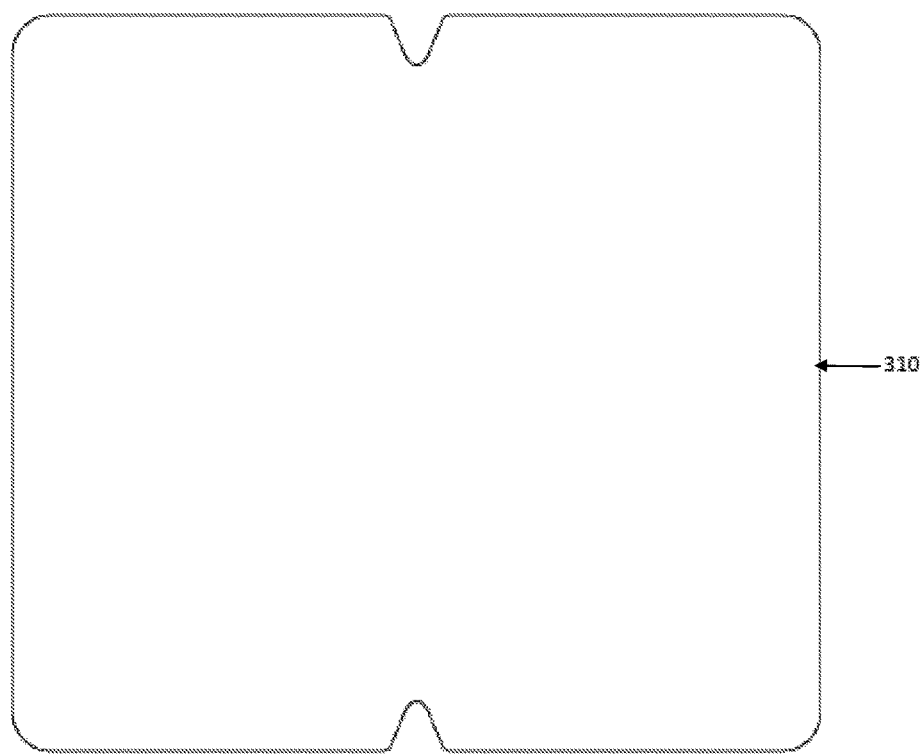
FIG. 33 is a front elevation of a membrane layer.

The valve membrane layer 310 is shown in FIG. 33. The valve membrane layer is a thin, flexible layer that is positioned adjacent the valve layer 300. The membrane is fluid tight and serves as a valve member either blocking flow across the valve seats 306 or permitting such flow. The valve membrane layer can be made of suitable materials such as silicone or polyurethane. The other layers can be made from suitable materials such as acrylic, polyethylene terephthalate-glycol modified (PETG), polycarbonate and polyetherimide. Other materials are possible. The valve membrane layer can have any thickness that provides the necessary flexibility and is suitable for the design and design dimensions of the particular application, for example 0.001 to 0.250" in thickness. The suitable materials of the valve membrane layer and the other layers that contact the fluid are impermeable to the fluid and non-reactive with the fluid. The layers can be bonded together with a suitable adhesive, fused together or mechanically connected. Other thicknesses are possible. Each of the valves 301 comprises corresponding portions of the valve layer 300 and the membrane layer 310.

Figure 34:
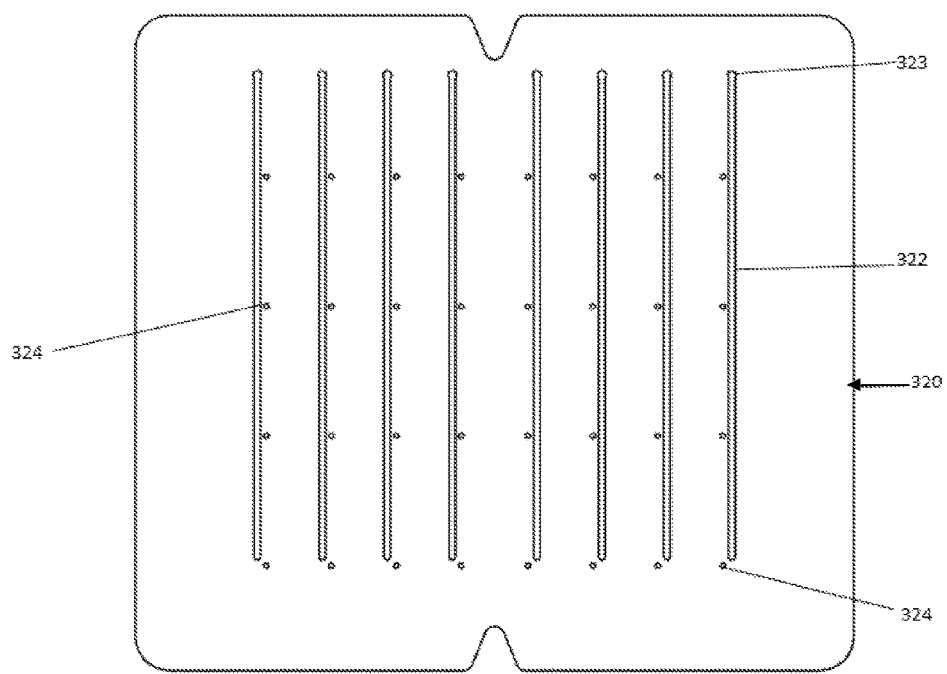
FIG. 34 is a front elevation of a fluid input channel layer.

The fluid input channel layer 320 is shown in FIG. 34. The fluid input channel layer 320 has a plurality of fluid input channels 322 formed as slots there through. The fluid input channels 322 receive fluid at inlet portions 323 and allow the fluid to travel through the length of the input channels 322. Adjacent portions of the valve membrane layer 310 and fluid via layer 330 seal and contain the fluid within the fluid input channels 322, which are slots in the fluid inlet channel layer 320. The fluid input channel layer 320 also includes a series of valve outlet openings 324 adjacent to the fluid input channels 322. As will be described in more detail, in operation fluid travels through the input channel 322 until it reaches an open valve 301. The valve membrane layer 310 in the vicinity of the valve 301 is locally pulled back into the valve seat 306 by the vacuum applied to the control gas channel 304 for that valve 301. The fluid then is permitted to flow from the fluid input channel 322, and across the open valve seat 306 in the space 312 formed by the valve channel 308 when the portion of the membrane layer 310 associated with the respective valve 301 and valve seat 306 is drawn into the valve channel 308 by the vacuum. The fluid flows in the space 312 between the rear face of the fluid input channel layer 322 and the pulled back portion of the valve membrane layer 310. The fluid flows through the space 312 until it reaches the location of the respective valve outlet opening 324 in the fluid input channel layer 320, and flows through the valve outlet opening. The opening of the valve 301 thereby diverts fluid flowing through the fluid input channel 322 to the respective valve outlet opening 324.

Figure 35:
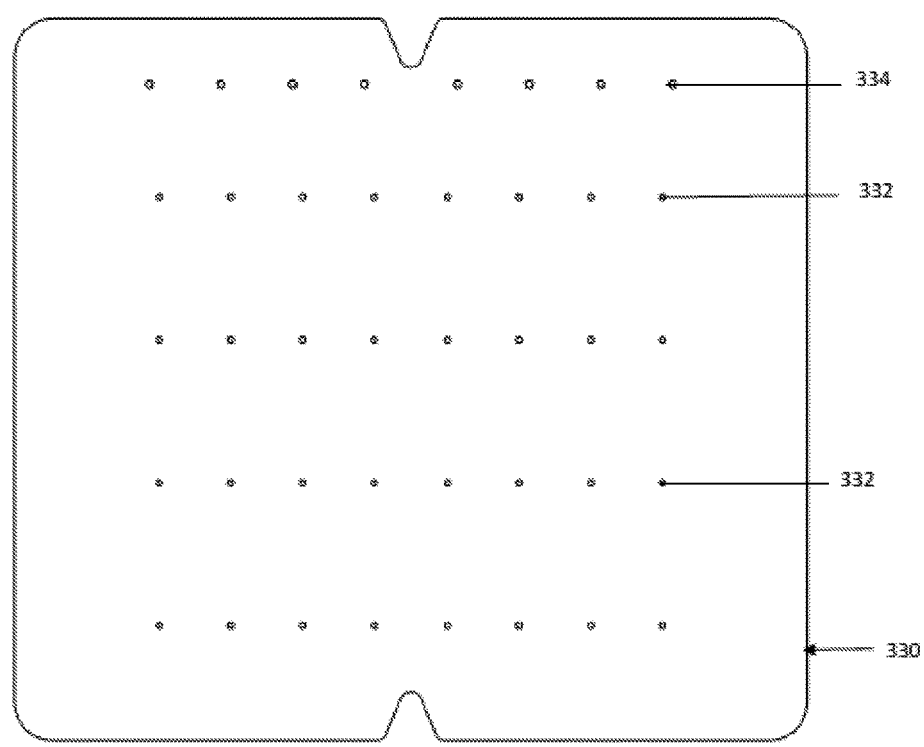
FIG. 35 is a front elevation of a fluid via layer.

A fluid via layer 330 is shown in FIG. 35. The fluid via layer 330 has a plurality of fluid input vias or openings 334, and a plurality of fluid output vias or openings 332. The fluid input vias 334 direct input fluid through the fluid via layer 330 to the inlet portions 323 of the fluid input channels 322 of the fluid input channel layer 320. The fluid output vias 332 receive fluid flowing through the valve outlet openings 324 of the fluid input channel layer 320 when an associated valve 301 is opened.

Figure 36:
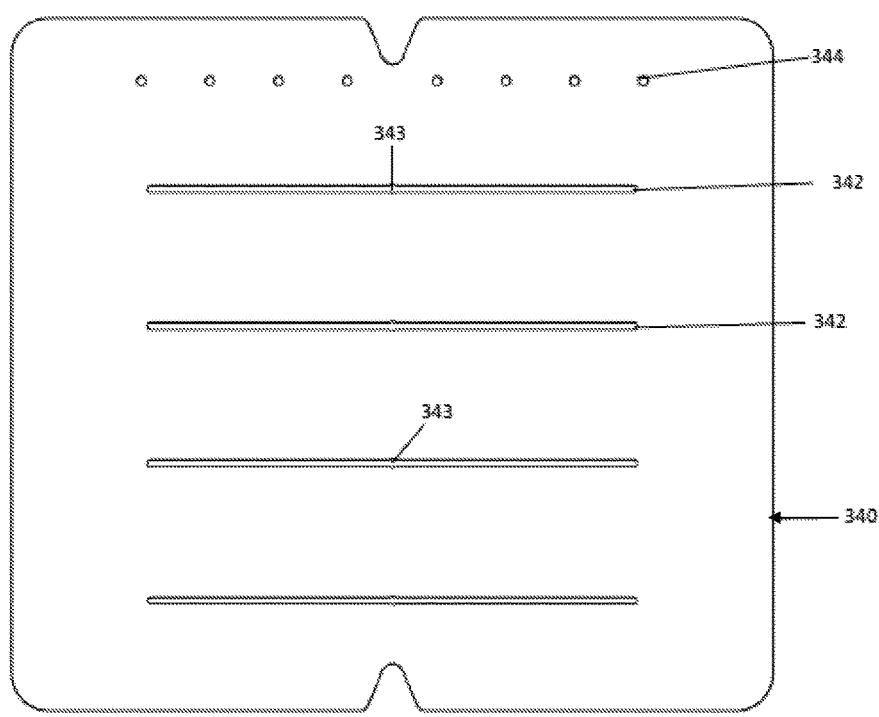
FIG. 36 is a front elevation of a fluid output channel layer.

A fluid output channel layer 340 is shown in FIG. 36. The fluid output channel layer 340 has a series of fluid input vias or openings 344 for directing input fluid to the fluid input vias 334 of the fluid via layer 330. The fluid output channel layer 340 also has a series of fluid output channels 342 formed as slots there through. The fluid output channels 342 receive output fluid from the fluid output vias 332 of the fluid via layer 330, and the fluid flows through the fluid output channels 342 to fluid outlet locations 343. Adjacent portions of the fluid via layer 330 and the fluid input/output layer 350 seal the fluid output channels 342.

Figure 37:
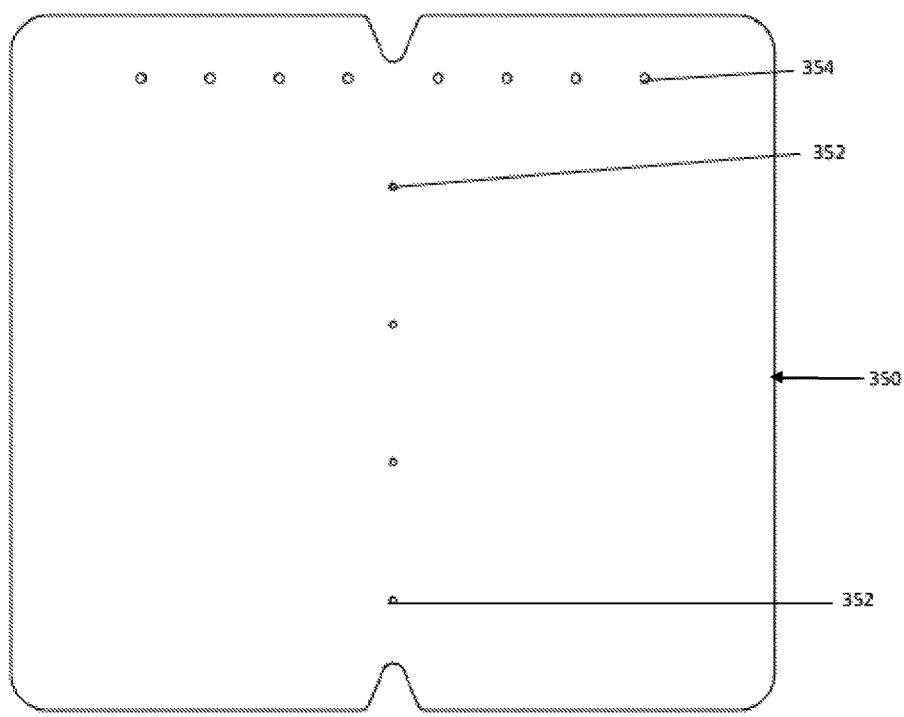
FIG. 37 is a front elevation of an input/output layer.

A fluid input/output layer 350 is shown in FIG. 37. The fluid input/output layer 350 includes a plurality of fluid input openings 354 which transmit input fluid to the fluid input vias 344 of the fluid output channel layer 340, and from there through the fluid input vias 334 of the fluid via layer 330 to the inlet portions 323 of the fluid input channels 322 of the fluid input channel layer 320. The fluid input/output layer 350 also includes a plurality of output openings 352 that receive fluid from the fluid outlet portions 343 of the fluid output channel layer 340.

Figure 38:
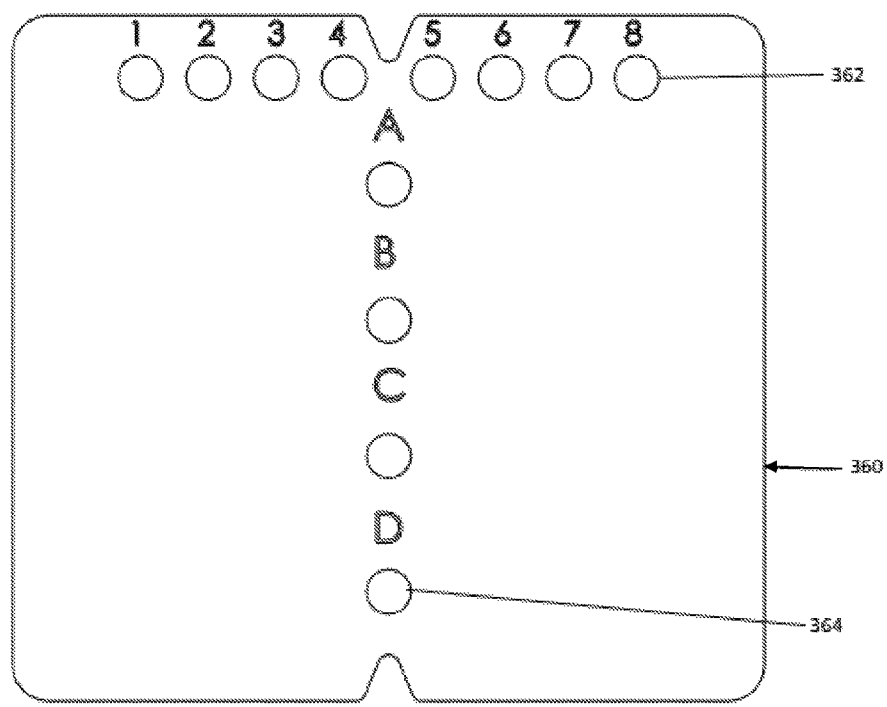
FIG. 38 is a front elevation of an outer layer for fittings.
Figure 39:
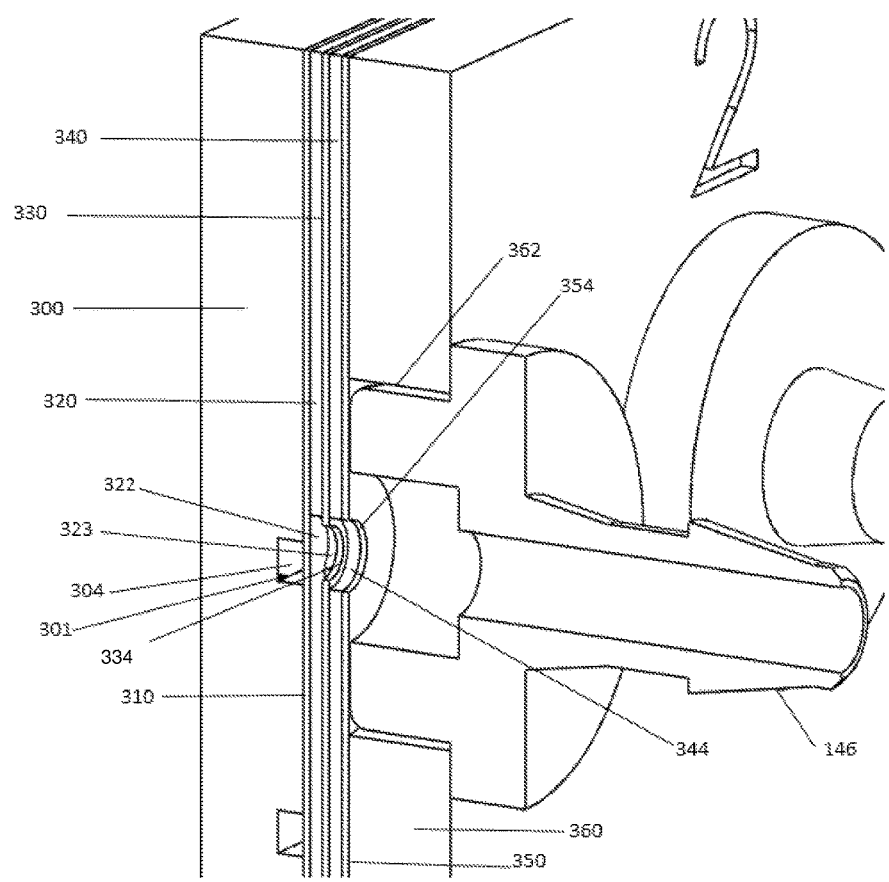
FIG. 39 is a cross-section through a portion of a fluidic manifold cartridge.
Figure 40:
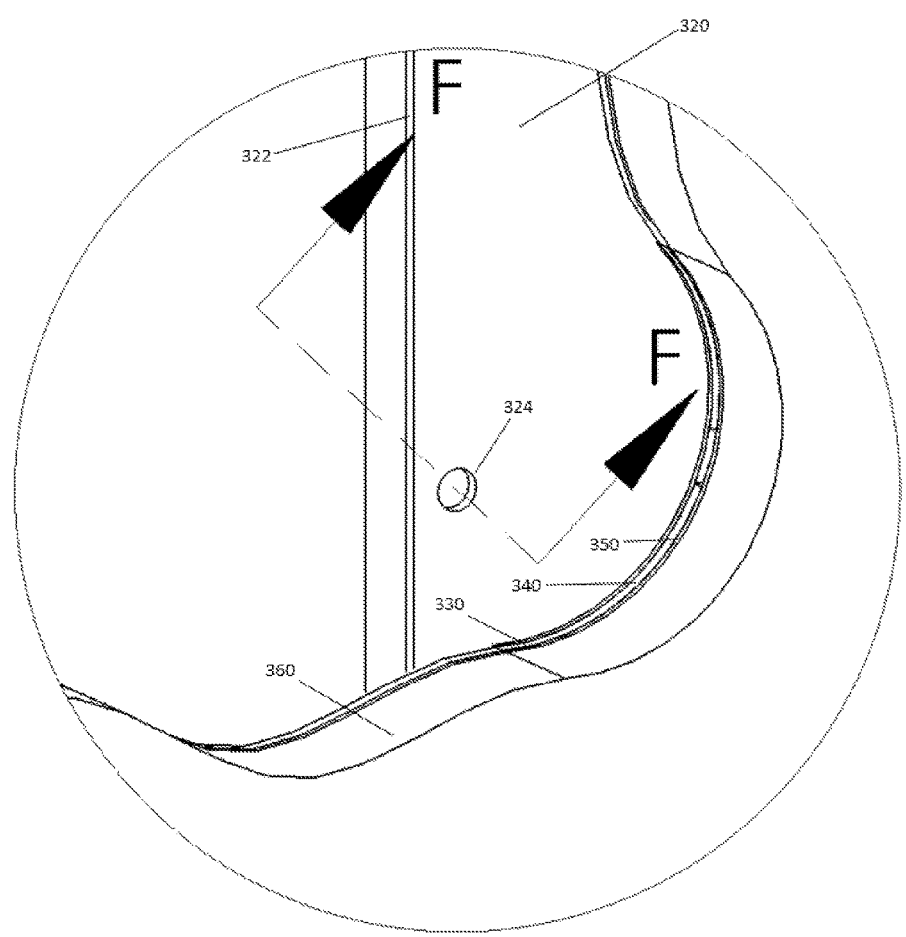
FIG. 40 is a perspective view partially broken away of a portion of a fluidic manifold cartridge.

An outer layer 360 is shown in FIG. 38. The outer layer 360 is provided to secure fluid input and output apparatus such as fluid input ports 146 and output ports 150. The outer layer 360 has port seats 362 for securing the fluid input ports 146, and directing this fluid through the outer layer 360 to the fluid input openings 354 of the fluid input/output layer 350. The outer layer 360 also has port seats 364 for securing the fluid output ports 150, and directing output fluid received from the output openings 352 of the fluid input/output layer 350 into output conduits secured to the output ports 150 such that output fluid will exit the cartridge 110. Other structure for directing output fluid from the cartridge 110 into output conduits is possible. Also, the outer layer 360 is not strictly required and fluid input and output structure such as ports or other structure could be provided to provide fluid communication with the fluid input openings 354 and fluid output openings 352 of the fluid input/output layer 350.

Figure 42:
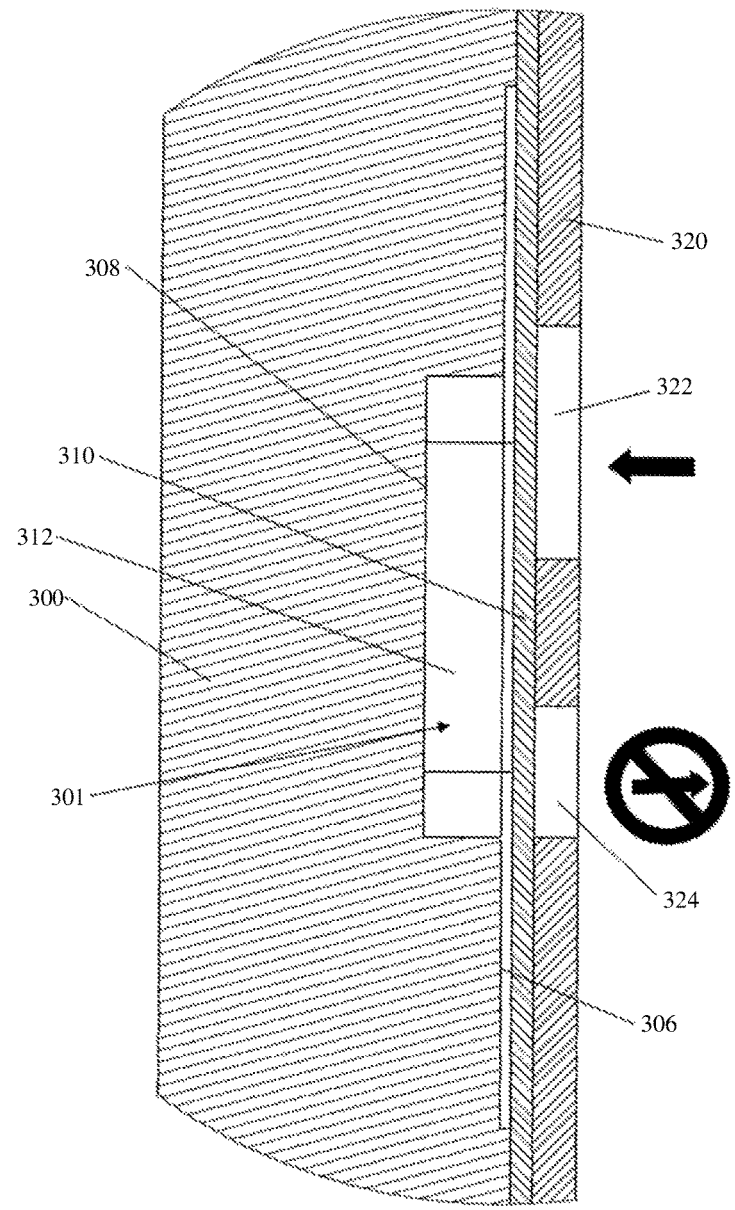
FIG. 42 is a cross-section taken along line F-F in FIG. 41, in a first mode of operation.
Figure 43:
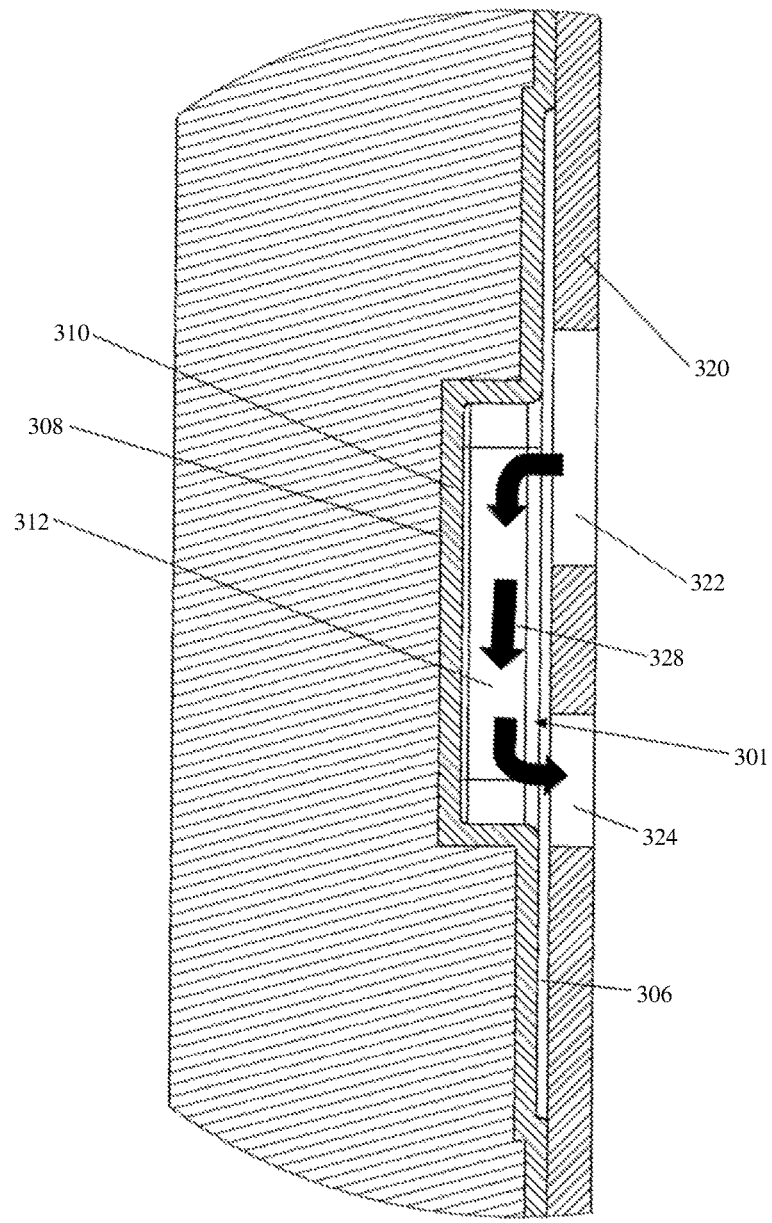
FIG. 43 is a cross-section, in a second mode of operation.
Figure 44:
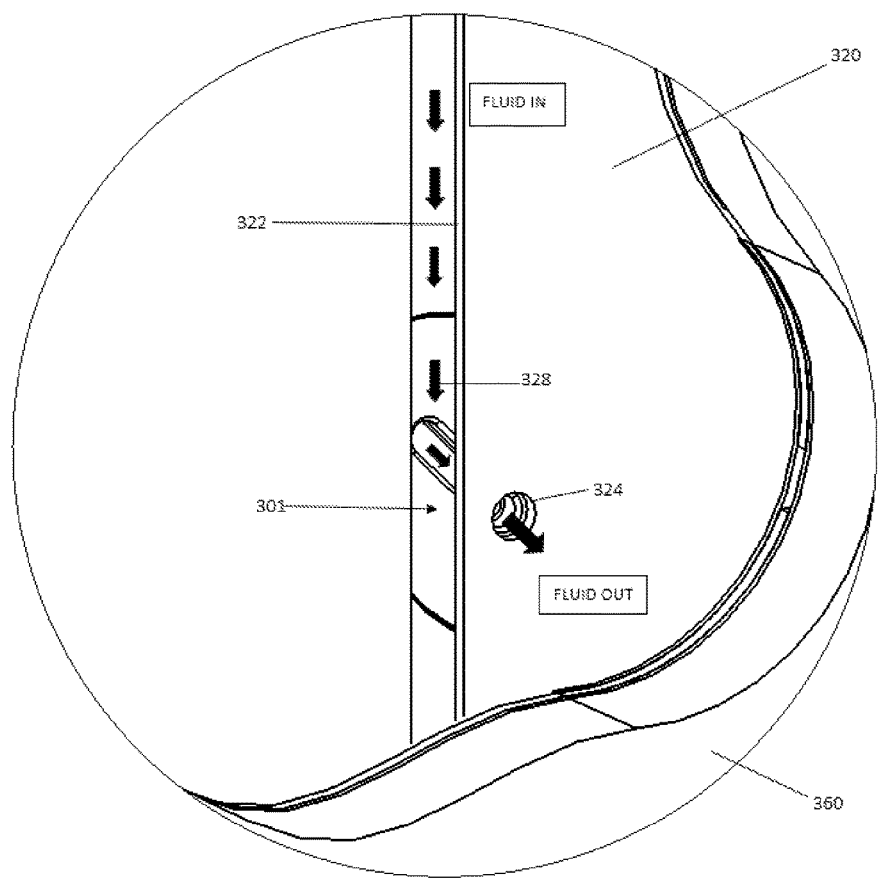
FIG. 44 is a perspective view, partially broken away in the second mode of operation.

The operation of the valves is based upon changes in control gas pressure communicated from the cartridge holder assembly 104 and the control gas manifold 130 to the cartridge 110. The manner in which this is accomplished and the construction of the valves can vary. An embodiment of the valves 301 illustrating operation is shown in FIGS. 39-44. Fluid flows through the fluid input channels 322 and past a series of valves 301 aligned with the fluid input channel 322. In the case where fluid is not to be redirected by a valve, control gas pressure in the control gas conduit 304 is neutral or positive such that the flexible membrane layer 310 remains in place or is forced by the positive pressure against the fluid input layer 320 (FIG. 42). The membrane layer 310 seals the fluid input channel 322 and does not permit fluid flowing through the fluid input channel 322 to flow out of the fluid input channel across the associated valve seat 306. Fluid flow is redirected by the valve 301 through operation of the programmable controller creating negative pressure (vacuum) through the control gas conduit 304. This will locally draw the flexible membrane layer 310 against the valve seat 306, and particularly the valve channel 308 (FIG. 43). Fluid will thereby be permitted to flow under the fluid input channel layer 320, through the space 312 above the valve channel 308 whereupon the fluid can exit through the fluid outlet opening 324 as indicated by arrows 328 in FIGS. 43-44. The valve 301 is closed by returning positive pressure to the control gas conduit 304, which will force the portion of the membrane 310 associated with the particular valve 301 to return to the closed position shown in FIG. 42.

Figure 45:
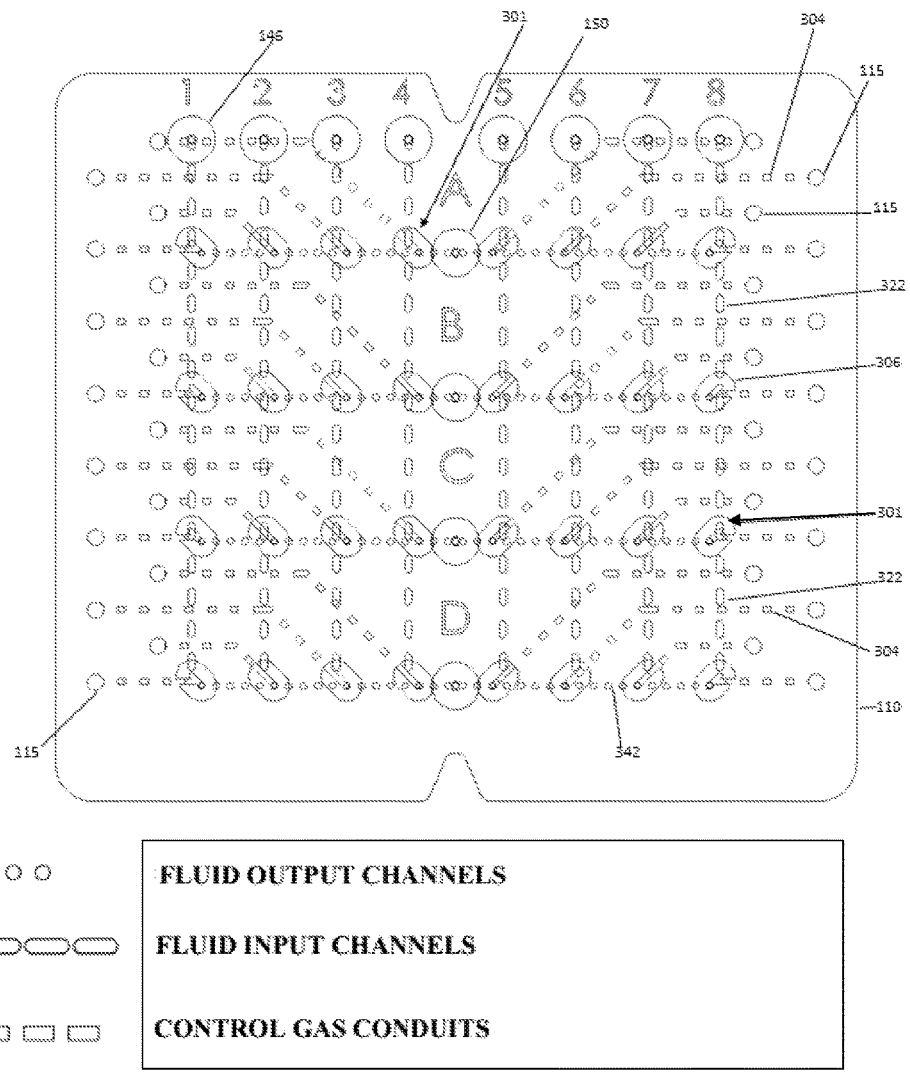
FIG. 45 is a schematic diagram illustrating possible fluid flow paths through the fluidic manifold cartridge.
Figure 46:
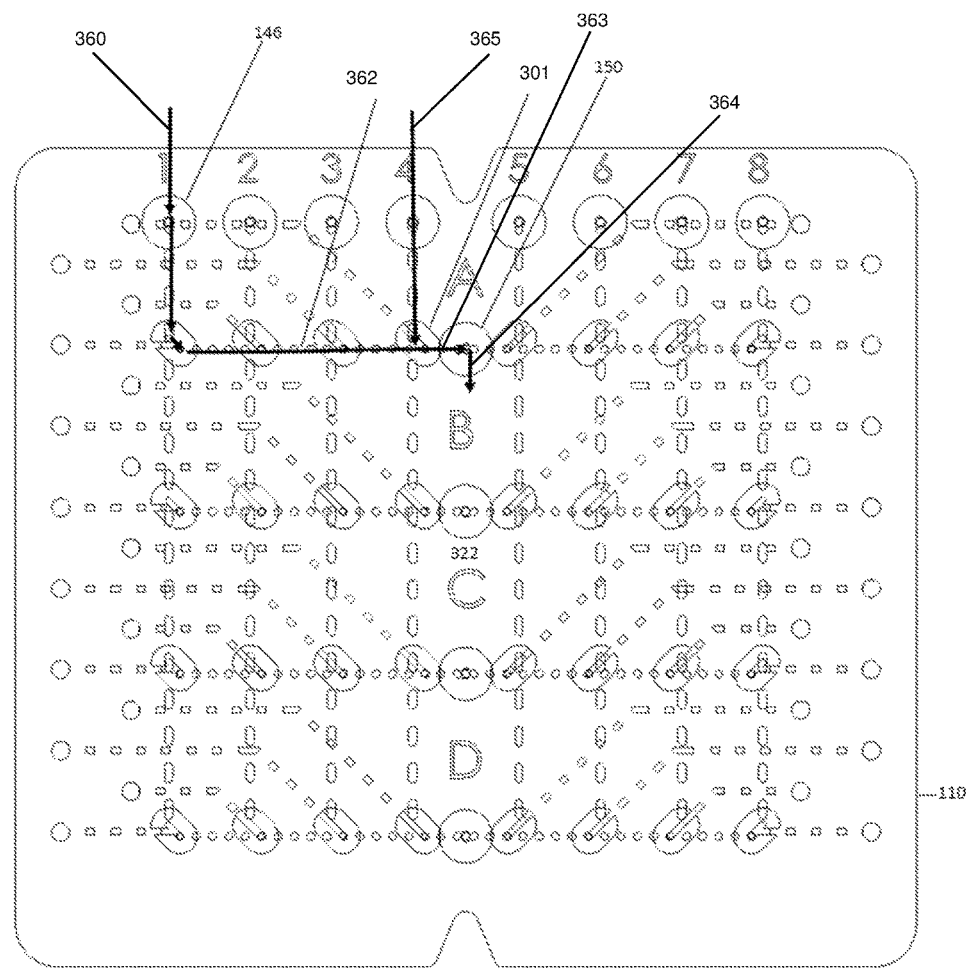
FIG. 46 a schematic diagram illustrating examples of fluid flow paths through the fluidic manifold cartridge.
Figure 47:
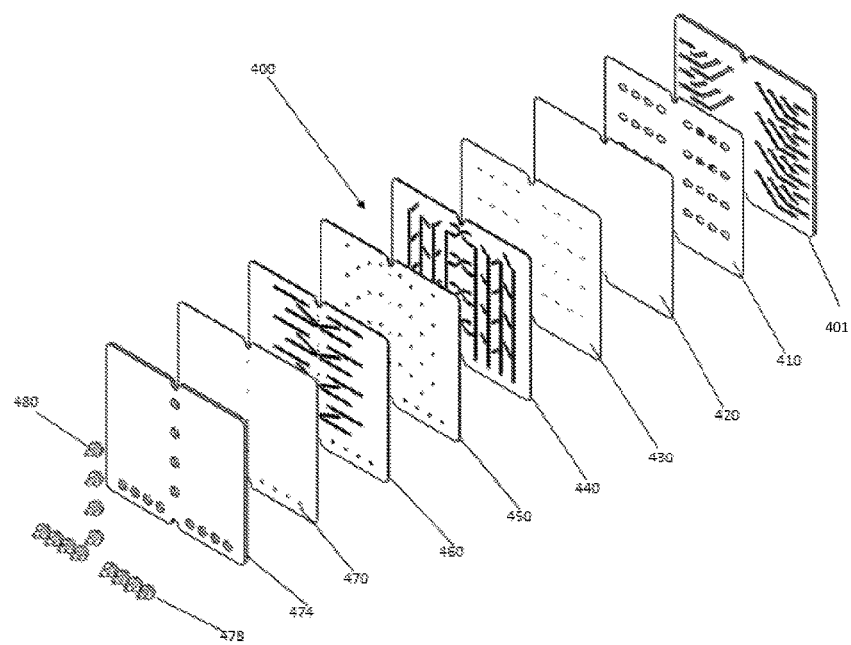
FIG. 47 is an exploded perspective view of a fixed dead volume fluidic manifold cartridge.
Figure 48:
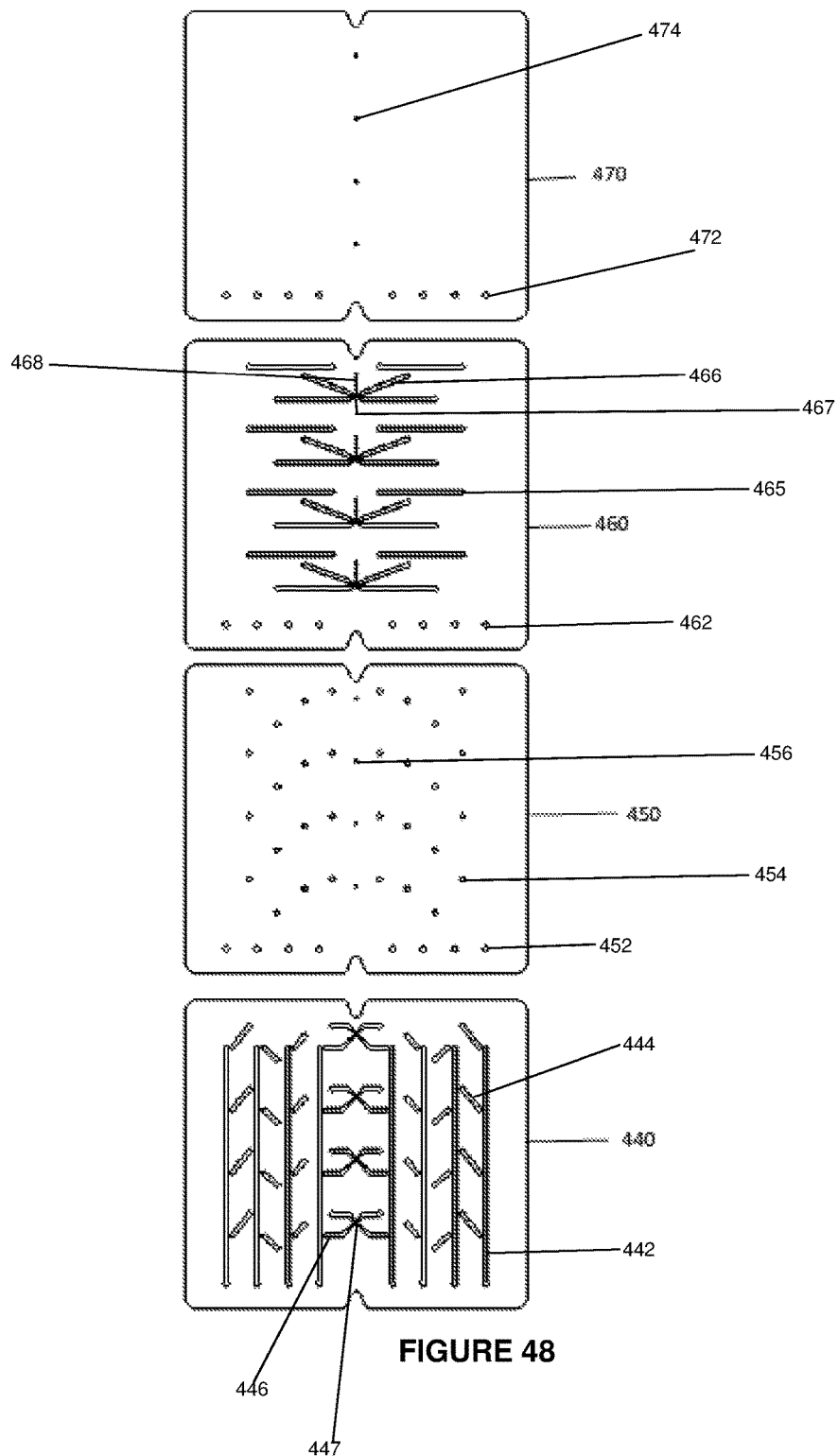
FIG. 48 is a front elevation of four layers of the fixed dead volume fluidic manifold cartridge.
Figure 49:
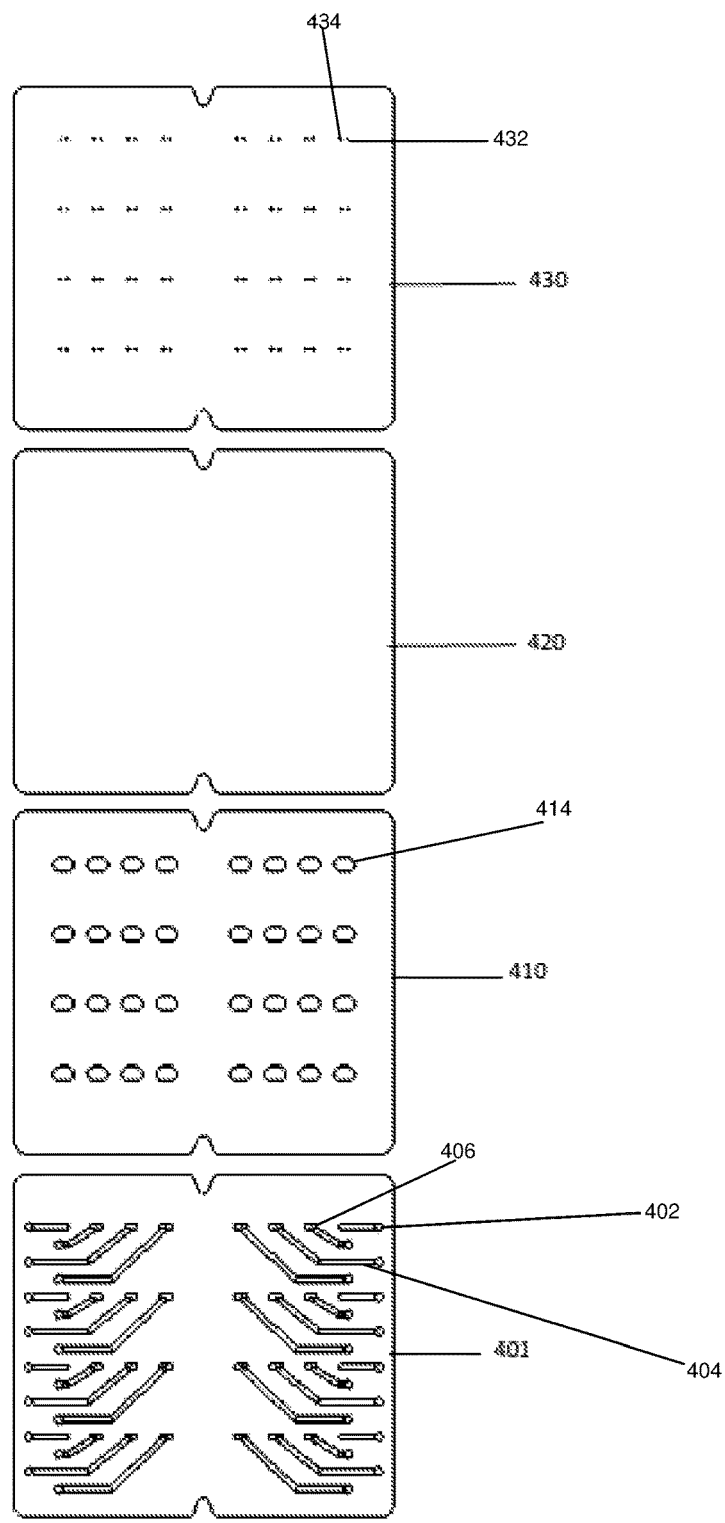
FIG. 49 is a front elevation of four additional layers of the fixed dead volume fluidic manifold cartridge.

A schematic depiction of the many possible flow paths available during the operation of the cartridge 110 is shown in FIGS. 45-46. The fluid input channels 322 in this embodiment are aligned vertically and the fluid output channels 342 are aligned horizontally, although other orientations are possible. The valves 301 serve to direct fluid where desired from a particular fluid input port 146 and associated fluid input channel 322, through a particular valve 301, to a particular fluid output channel 342 and out a desired output port 150 to a designated sample container 114 (not shown).

There is shown in FIG. 46 two possible flows through the cartridge 110. The first flow 360 from Input 1 is redirected by the first valve that it encounters to a flow path 362 toward an exit flow from the cartridge 110 as indicated by arrow 364. A second flow 365 from Input 2 also exits the cartridge 110 through the same flow path 364. Both flow paths must traverse the leg 363, however, only the flow path from Input 1 must traverse the additional distance indicated by flow path 362. This is referred to as a "variable dead volume"—the additional volume of fluid in flow path 362 must be accounted for when Input 1 is used as compared to Input 4. Input 1 has a dead volume comprised of flow paths 362 and 363, while Input 4 has a dead volume comprising only flow path 363.

There is shown in FIGS. 47-55 a cartridge 400 which provides a perfusion manifold with a "fixed" dead volume. This means that the liquid residence time in the cartridge 400 will remain the same no matter which flow path the fluid takes within the cartridge 400. The cartridge 400 includes a control fluid opening layer 401, a valve layer 410, a membrane layer 420, a fluid valve input/out opening layer 430, a fluid input channel layer 440, a fluid via layer 450, a fluid output channel layer 460, and a cartridge fluid input/output layer 470. An outer layer 474 with fluid input ports 478 and fluid output ports 480 can also be provided.

Figure 50:
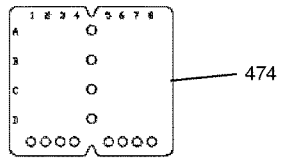
FIG. 50 is a comparison of a variable dead volume fluidic manifold cartridge layers and a fixed dead volume fluidic manifold cartridge layers.
Figure 50:
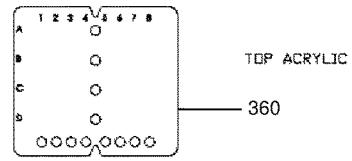
Figure 50:
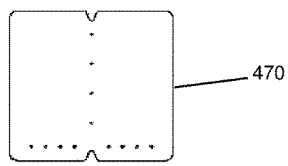
Figure 50:
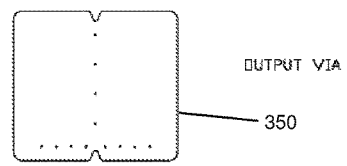
Figure 50:
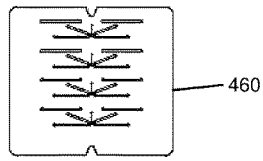
Figure 50:
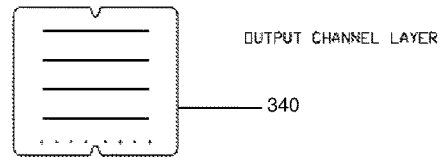
Figure 50:
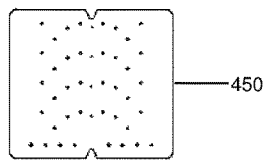
Figure 50:
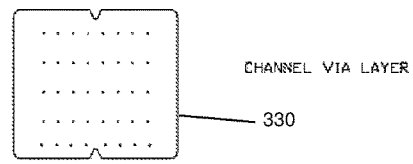
Figure 50:
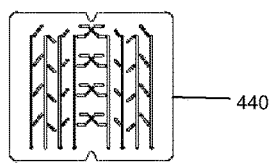
Figure 50:
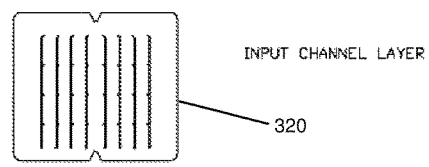
Figure 50:
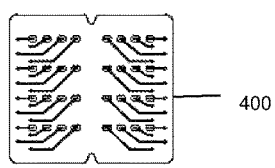
Figure 50:
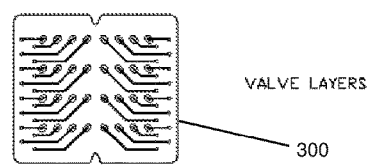
Figure 51:
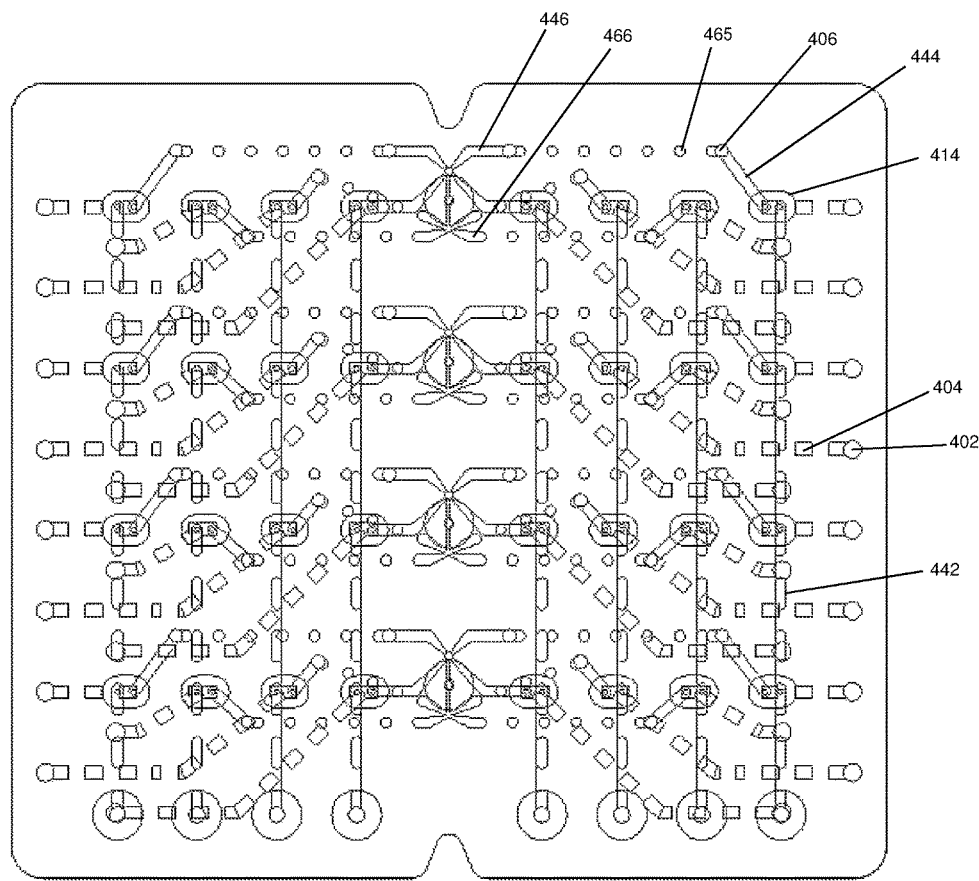
FIG. 51 is a schematic diagram illustrating possible fluid flow paths through a fixed dead volume fluidic manifold cartridge.
Figure 52:
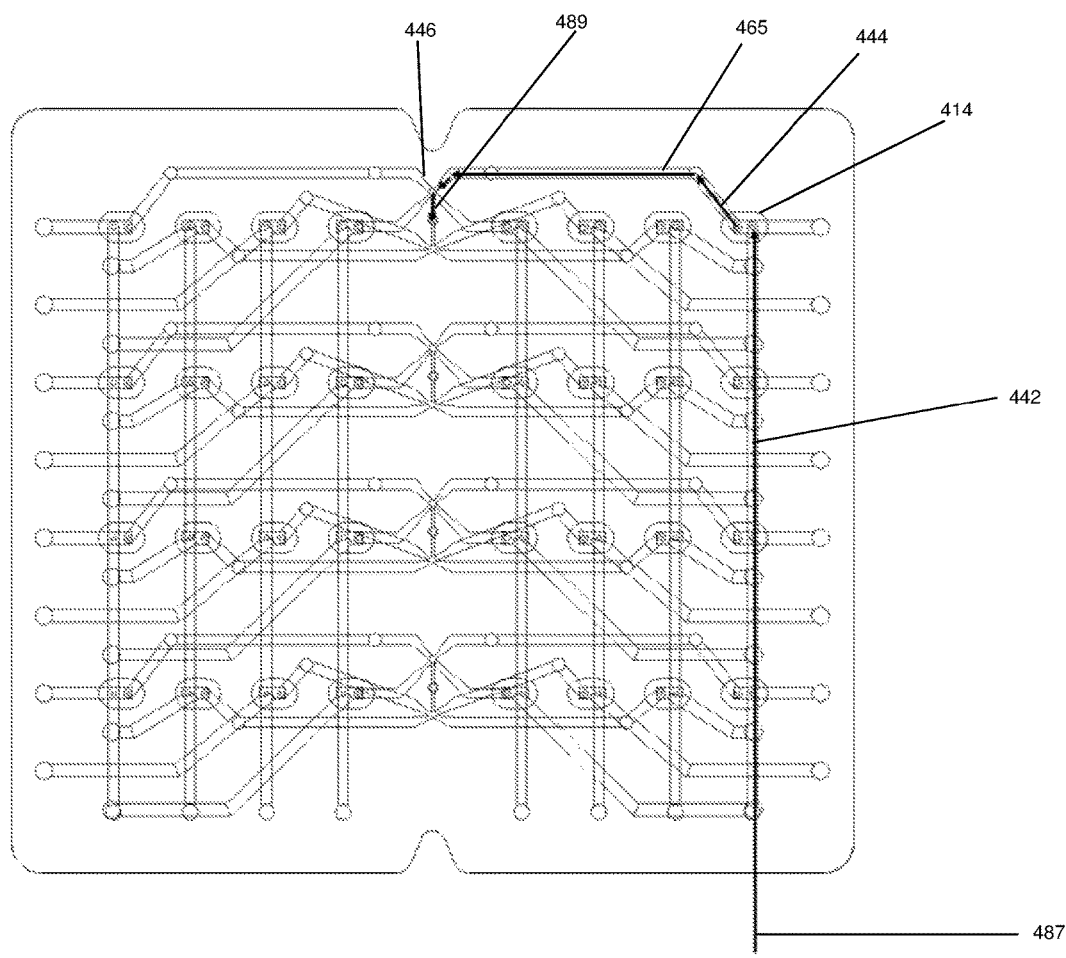
FIG. 52 is a schematic diagram of a possible fluid flow path through the fixed dead volume fluidic manifold cartridge.
Figure 53:
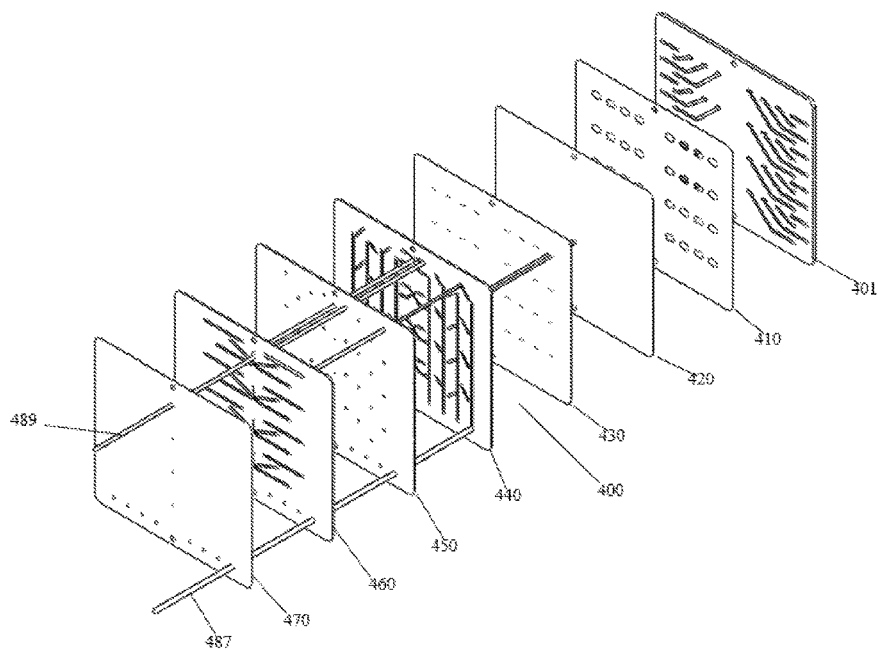
FIG. 53 is an exploded perspective view of the fluid flow path of FIG. 52.
Figure 54:
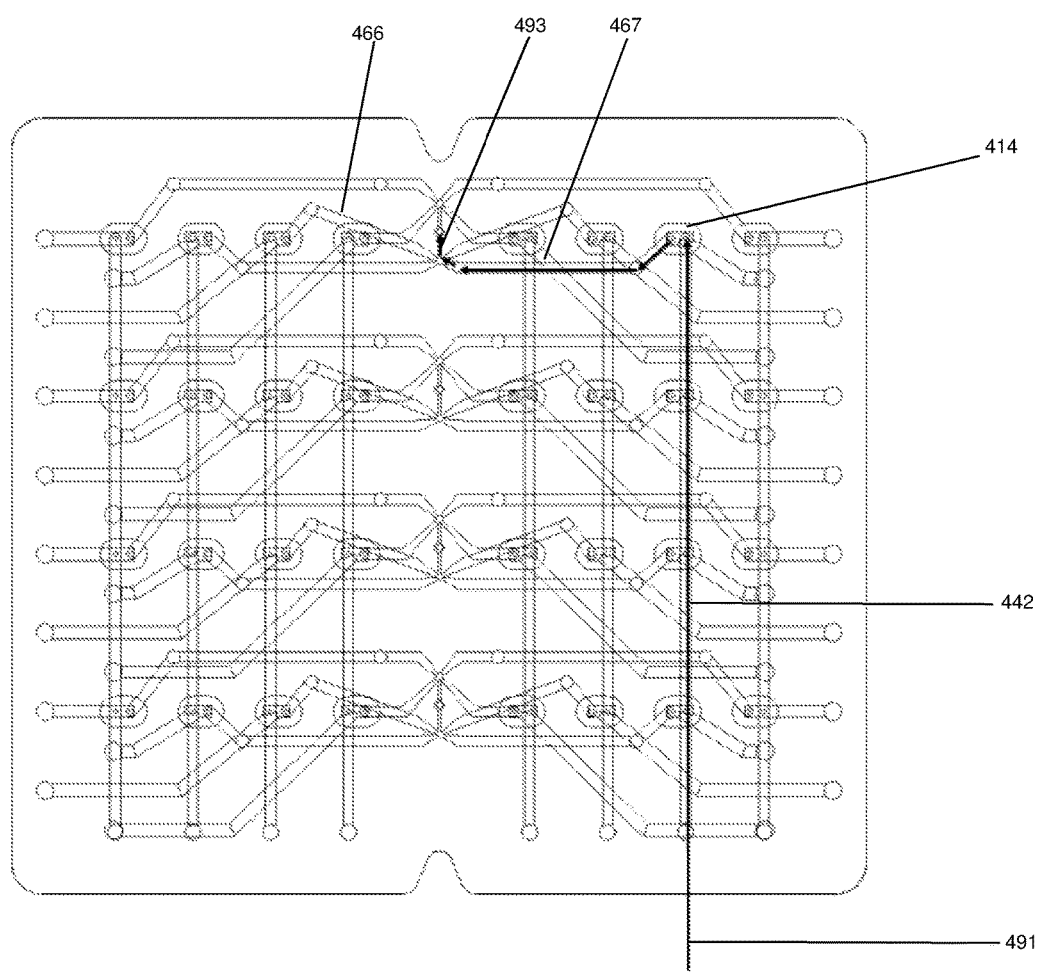
FIG. 54 is a schematic diagram of alternative possible fluid flow path through the fixed dead volume fluidic manifold cartridge.
Figure 55:
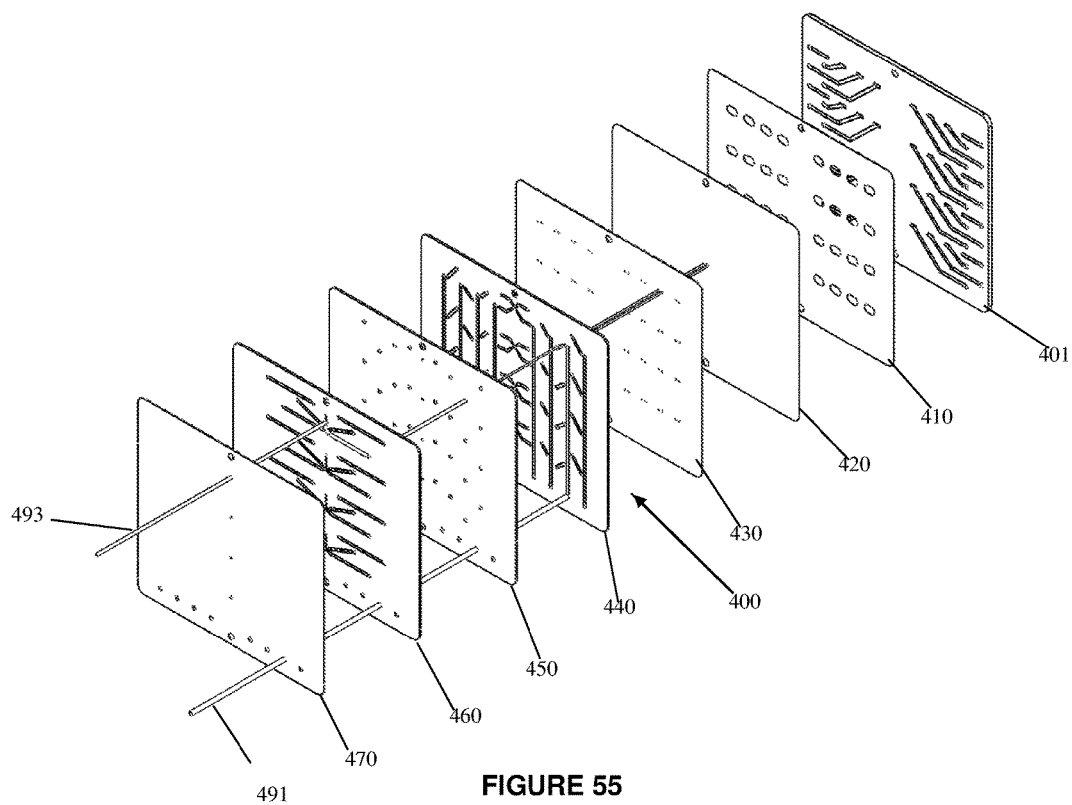
FIG. 55 is an exploded perspective view of the fluid flow path of FIG. 54.
Figure 56:
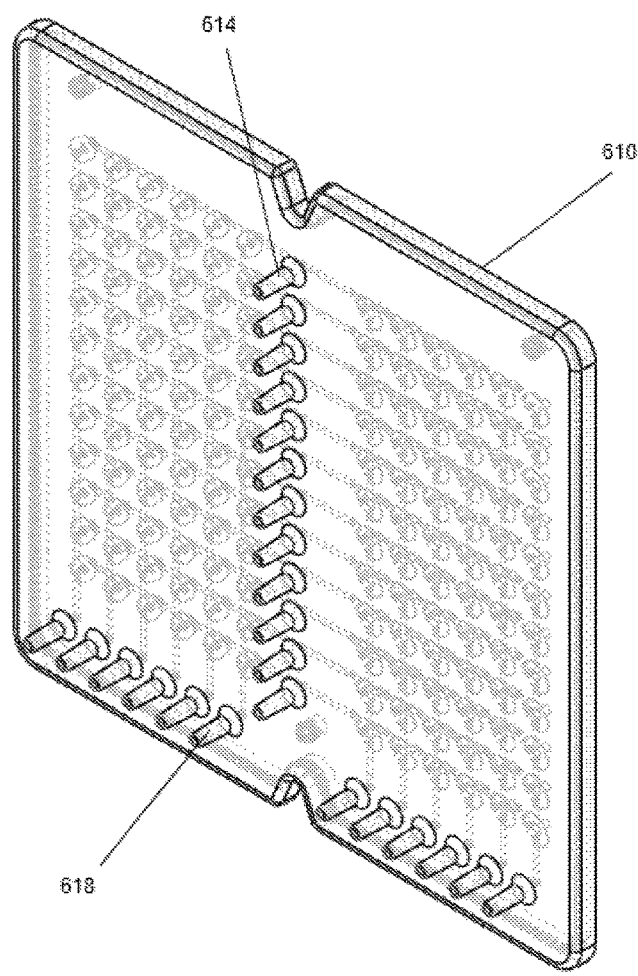
FIG. 56 is a perspective view of a 12×12-fluidic manifold cartridge, partially in phantom.
Figure 57:
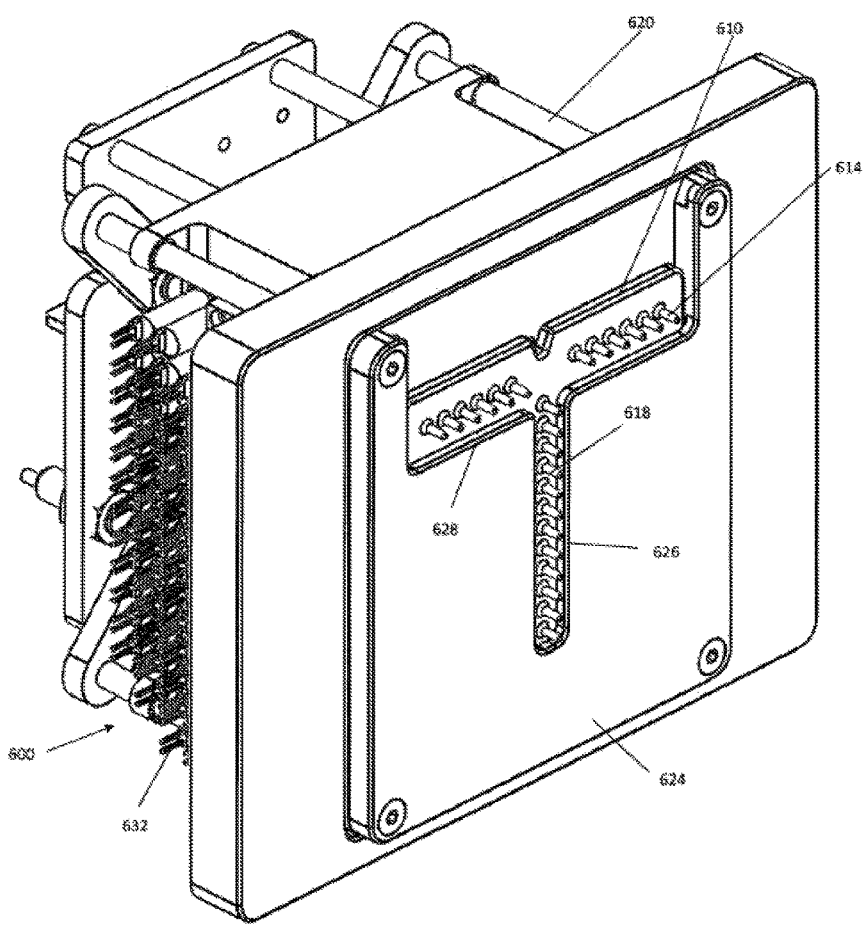
FIG. 57 is a perspective view of a 12×12-fluidic manifold cartridge holder assembly with a 12×12-fluidic manifold cartridge.
Figure 58:
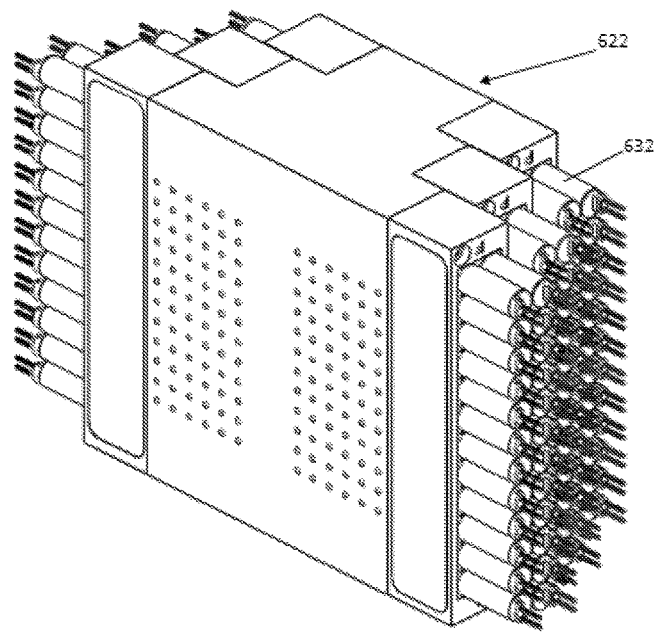
FIG. 58 is a front perspective view of a 12×12-fluidic manifold cartridge control valve assembly.
Figure 59:
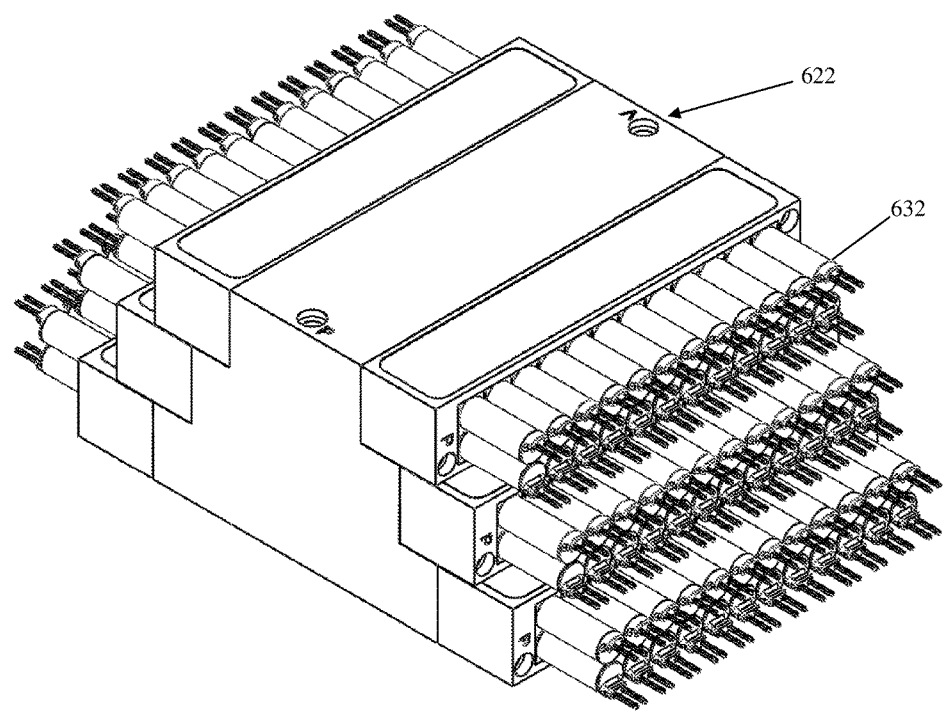
FIG. 59 is a rear perspective.

The fixed dead volume cartridge 400 can be constructed in layers as described for the variable dead volume cartridge 110, and flows through each cartridge are in many respects similar. A comparison of the layers of the two cartridges is shown in FIG. 50. A schematic diagram illustrating flow paths through the fixed dead volume cartridge 400 is shown in FIG. 51. Fluid flows through the input channels 442 in the fluid input channel layer 440 past the location of the valves 414 associated with that input channel 442. Upon operation of a valve 414, fluid flows through the associated valve input/output openings in the valve input/output opening layer 430. At this point, the fluid has two possible paths depending on the associated valve 414. As shown in FIGS. 52-53, the fluid input 487 can throw flow through channel 442 in fluid input channel layer 440, through channel 465 in the fluid output channel layer 460, and through openings in the fluid via layer to a manifold 446 formed in the fluid input channel layer 440 and exits as output flow 489. Alternatively, and as shown in FIGS. 54-55, the fluid input 491 can pass through the fluid via layer 450 to the fluid output channel layer 460, and flow through channel 467 and an alternate manifold 466 formed in the fluid output channel layer 460 and exits as output flow 493. Both paths exit through outlet openings in the cartridge fluid input/output layer 470.

The fluidic manifold cartridge of the invention can be scaled to different numbers of fluid inputs and fluid outputs. There is shown in FIGS. 56-69 a fluidic manifold system 600 with a cartridge 610 that is designed for 12 fluid inputs and 12 fluid outputs. The 12×12 fluidic manifold cartridge 610 can have fluid input ports 618 and fluid output ports 614. A fluidic manifold cartridge holder assembly 620 includes a control gas manifold 622 and a clamp 624 for securing the cartridge 610 in position. The clamp 624 includes a vertical slot 626 and horizontal slot 628 to permit access to the fluid input ports 618 and fluid output port 614. Other designs are possible. The control gas manifold 620 also includes a plurality of control gas valves 632 which are operable by a programmable controller (not shown). Operation of the clamp 624 is provided by a suitable structure such as solenoid which suitable structure such as a gear (not shown) to drive the manifold 620 and clamp 624 together and secure the cartridge 610.

Figure 60:
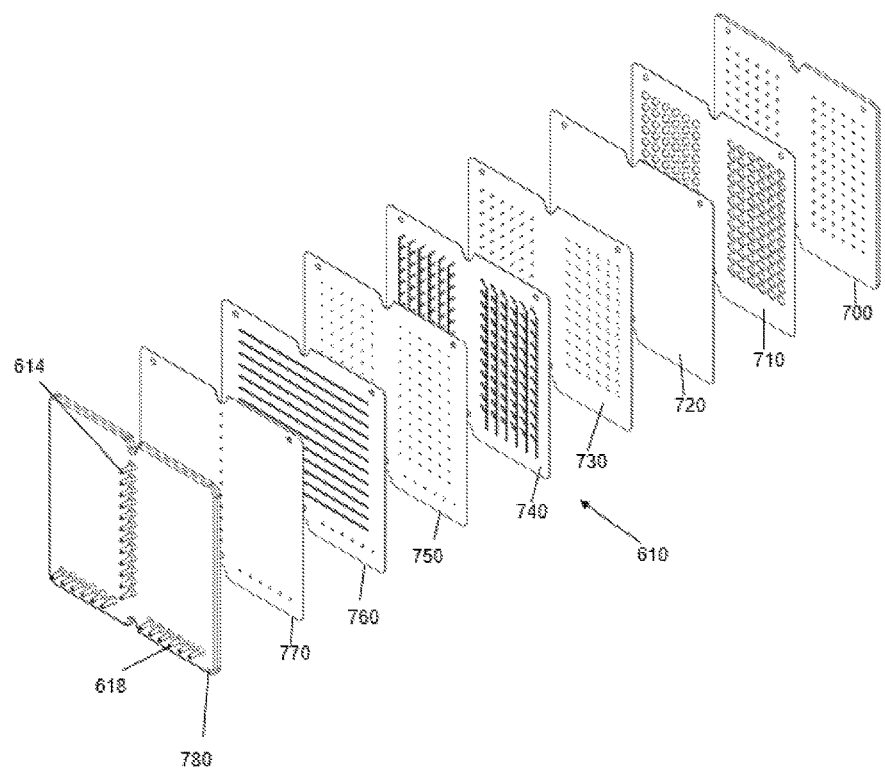
FIG. 60 is an exploded perspective of a 12×12-fluidic manifold cartridge.
Figure 61:
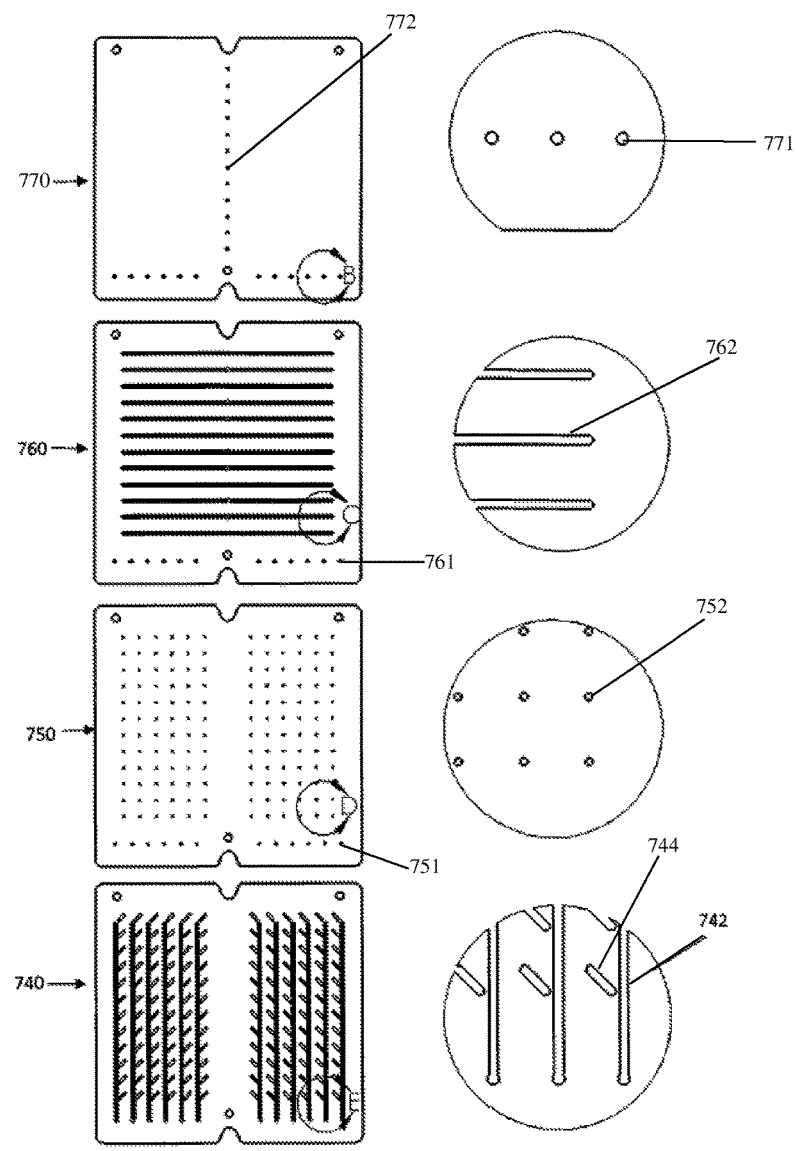
FIG. 61 is a plan elevation of a four layers of a 12×12-fluidic manifold cartridge and enlarged areas B, C, D, and E.
Figure 62:
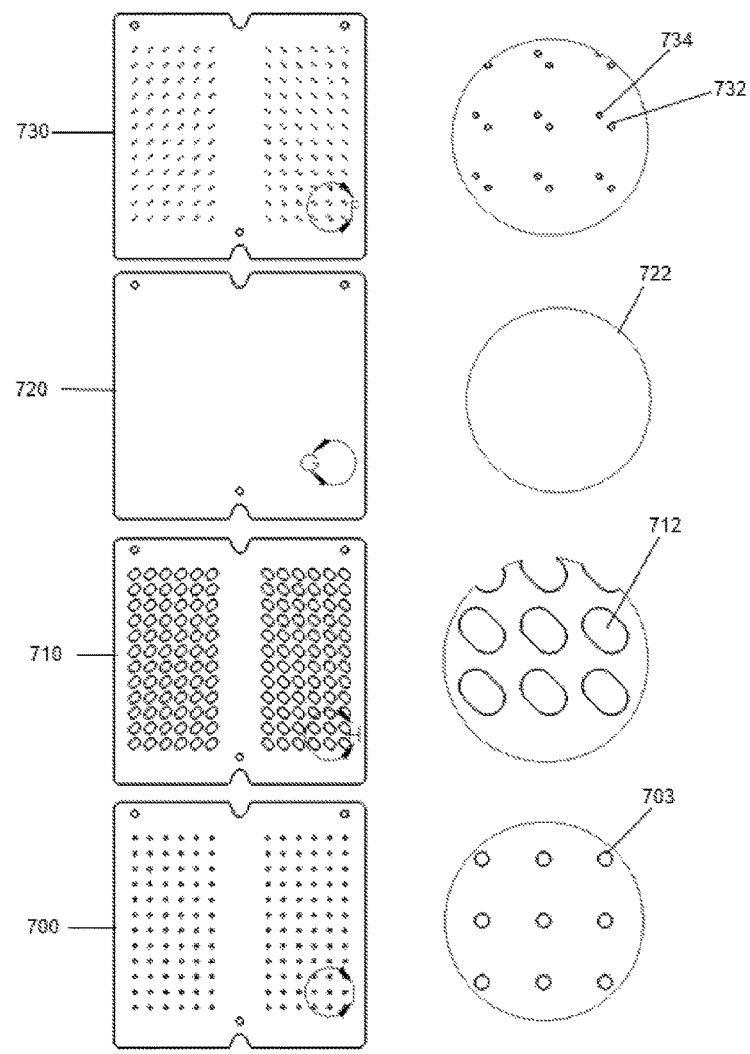
FIG. 62 is a plan elevation of four additional layers of the 12×12-fluidic manifold cartridge and respective enlarged areas F, G, H and I.
Figure 63:
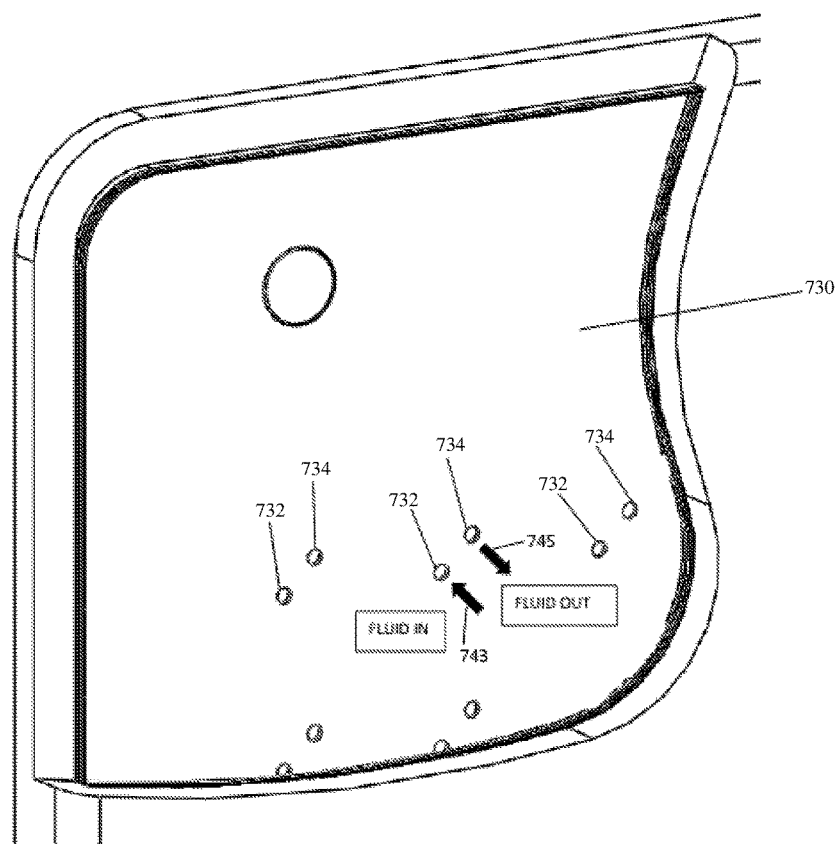
FIG. 63 is a perspective view, partially broken away, of the fluidic manifold cartridge and a fluid inlet/outlet layer.
Figure 64:
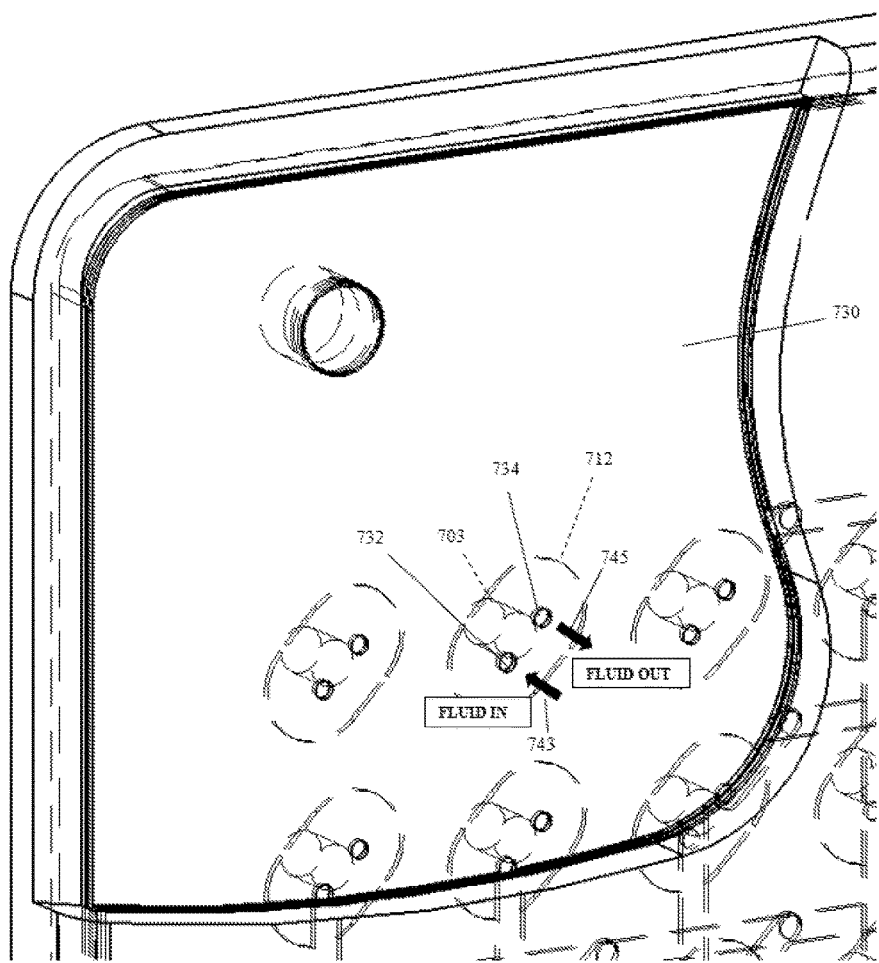
FIG. 64 is a perspective view, partially broken away and partially in phantom, of the fluidic manifold cartridge and the fluid inlet/outlet layer.

There is shown in FIGS. 60-62 an exploded perspective and layers of the 12×12 cartridge 610. The layers include the control fluid opening layer 700 with control fluid openings 703. A valve layer 710 has valve seats 712. A membrane layer 720 has portions 722 associated with the location of each valve. A fluid valve input/output opening layer 730 has valve inlet openings 732 and valve outlet openings 734. A fluid input channel layer 740 has fluid input channels 742 and fluid valve output channels 744. A fluid via layer 750 has fluid output vias 752. A fluid output channel layer 760 has output channels 762. A cartridge fluid input/output layer 770 has input openings 771 and output openings 772. An outer layer 780 for input and output ports can also be provided.

Fluid entering the cartridge through the input ports 618 is directed to the inlet openings 771 of the fluid input/output layer 770. Fluid leaving the cartridge through output openings 772 is directed to the outlet ports 614.

The fluid output channel layer 760 comprises fluid input openings 761 and a plurality of fluid output channels 762. The fluid input openings 761 receive fluid from the input openings 771 of the fluid input/output layer 770. The fluid output channels 762 direct fluid to the center position where the fluid can escape through the output openings 772 of the fluid input/output layer 770.

The fluid via layer 750 includes fluid input vias 751 and fluid output vias 752. The fluid input vias 751 direct fluid to the fluid input channel layer 740. The fluid output vias 752 receive fluid from the fluid input channel layer 740 and direct the fluid to the fluid output channels 772 of the fluid output channel layer 770.

The fluid input channel layer 740 includes fluid input channels 742 and fluid output valve channels 744. The fluid input channels 742 receive fluid from the fluid input vias 751 of the fluid via layer 750. The fluid flows through the fluid input channels 742 past several of valves with valve inlet openings 732 aligned with each fluid input channel 742. The valve output channels 744 receive fluid from the valves and direct this fluid to the fluid output vias 752.

The valve inlet/outlet opening layer 730 includes valve inlet openings 732 and valve outlet openings 734. The valve inlet openings 732 and valve outlet openings 734 work combination with the valve membrane layer 720 in the manner to be described.

The valve membrane layer 720 performs the function of a valve member. Movement of a portion 722 of the valve membrane 720 corresponding to a particular valve operates the valve between the open and closed positions. The portion 722 of the membrane 720 moves into the valve seat 712 upon the application of control gas through the control gas openings 703.

The valve layer 710 includes a plurality of valve seats 712. The valve seats 712 operate as previously described by receiving corresponding portions 722 of the valve membrane 720 to open and close the respective valve.

The control fluid opening layer 700 includes a number of control fluid openings 703. The control fluid openings 703 receive fluid in the manner previously described to retract the corresponding portions 722 of the valve membrane 720 to open and close the valve.

Figure 65:
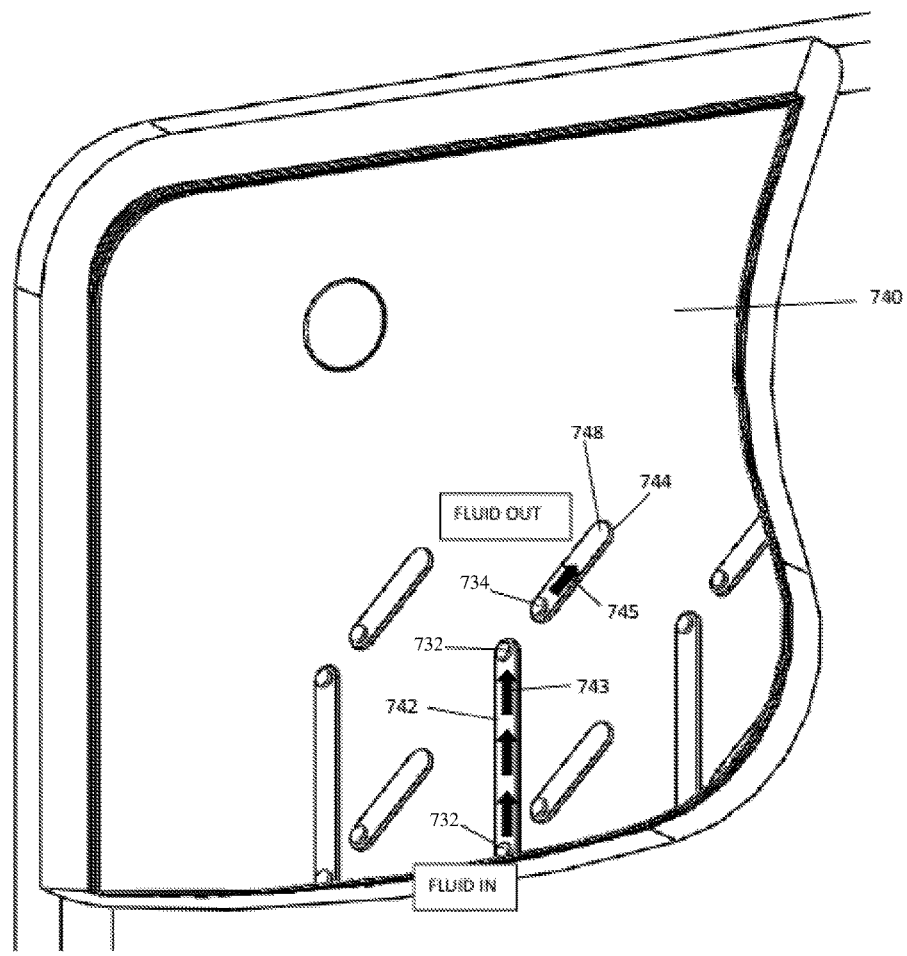
FIG. 65 is a perspective view, partially broken away, of the 12×12-fluidic manifold cartridge and a fluid inlet flow channel layer.
Figure 66:
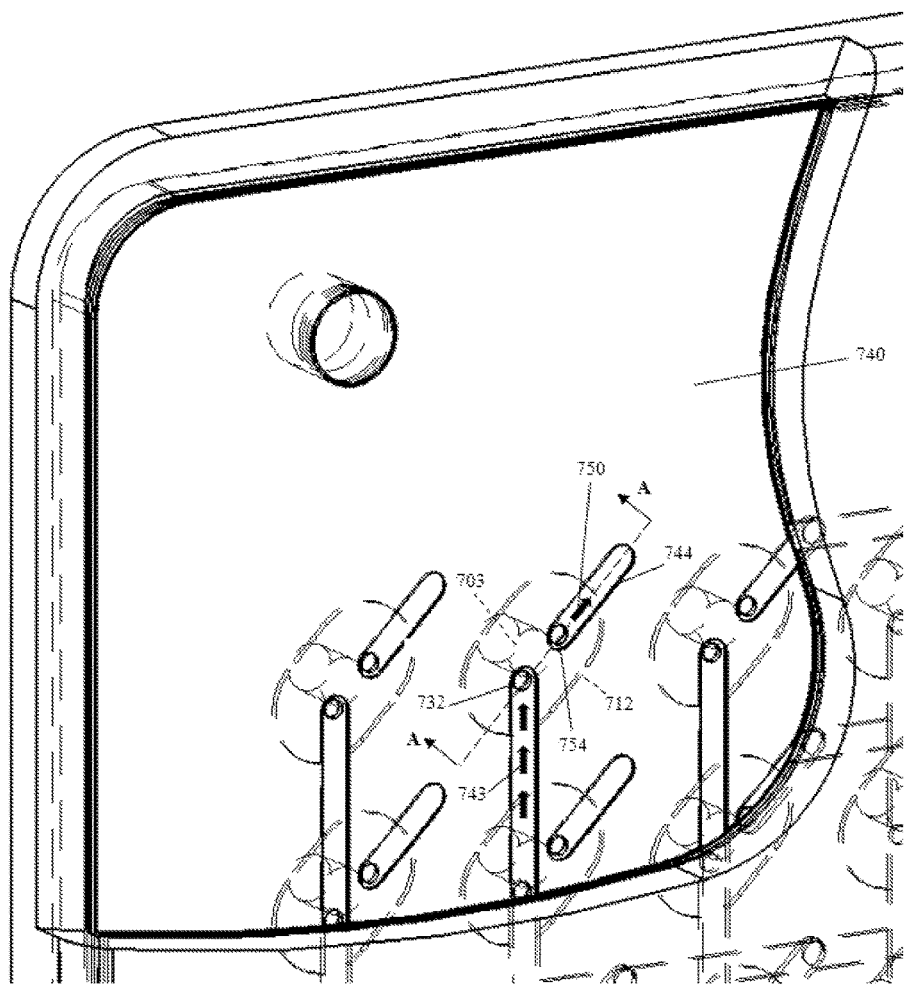
FIG. 66 is a perspective view, partially broken away and partially in phantom, of the 12×12-fluidic manifold cartridge and the fluid inlet flow channel layer.
Figure 67:
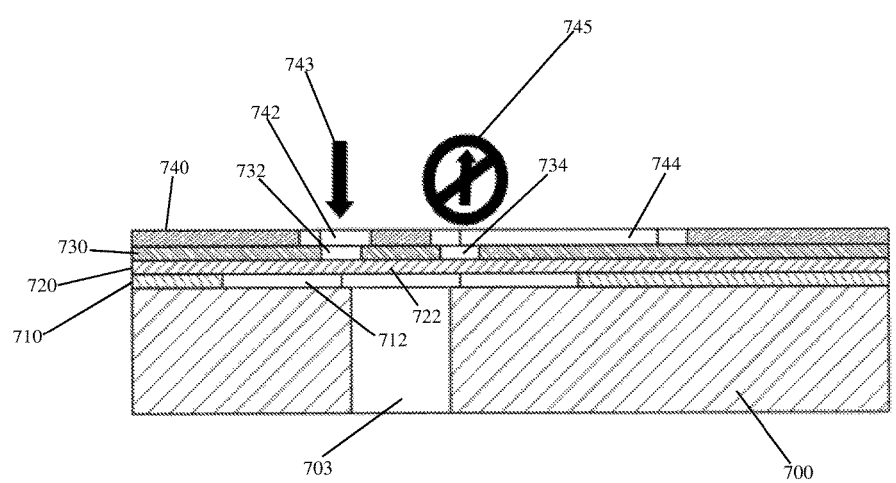
FIG. 67 is a cross-section taken along line A-A in FIG. 66 in a first mode of operation.
Figure 68:
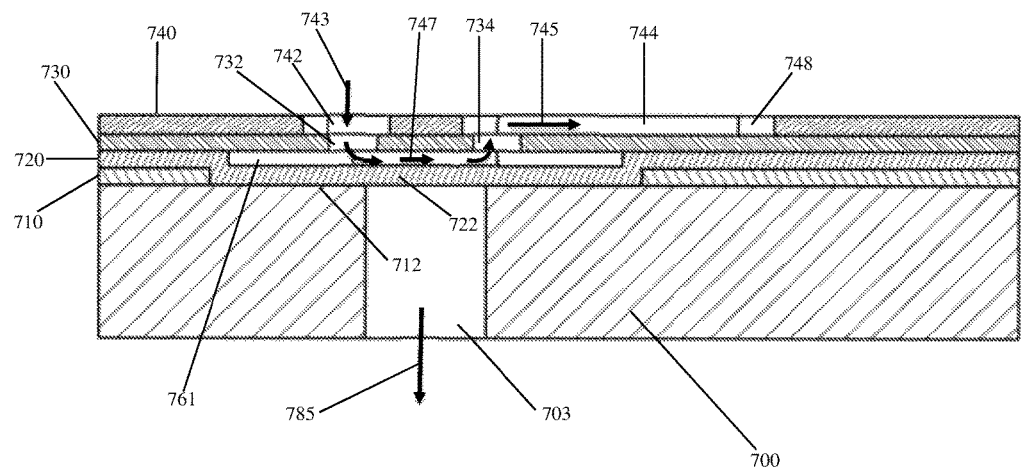
FIG. 68 is a cross-section taken along line A-A in FIG. 66 in a second mode of operation.

Operation of the valve is shown in FIGS. 63-68. Fluid enters through the fluid inlet openings 732 and exits the valve outlet openings 734 of the valve inlet/outlet opening layer 730. As shown in FIG. 65, the fluid flows (arrow 743) through the valve input channel 742 of the fluid input channel layer 740 past a plurality of fluid inlet openings 732. As shown in FIG. 67, the valve will remain closed if there is suitable control gas pressure delivered to the control gas opening 703 of the respective valve. The corresponding portions 722 of the valve membrane layer 720 will remain in place blocking flow into the fluid inlet openings 732 and out of the fluid outlet openings 734 (arrow 745) of the valve inlet/outlet opening layer 730.

Upon the appropriate control gas signal reaching the control gas opening 703 (arrow 785, FIG. 68), the corresponding portions 722 of the membrane layer 720 will be drawn into the valve seats 712 to create a flow space 761 between the corresponding portions 722 and the fluid inlet opening 732 and fluid outlet openings 734. This will permit the input flow of fluid (arrow 743) to flow through the inlet opening 732 and the space 761 (arrow 747) and out the fluid outlet opening 734. Fluid leaving the fluid outlet openings 734 will reach the fluid valve output channel 744 until it reaches a location 748 which corresponds to the location of the respective fluid output via 752 of the fluid via layer 750.

Figure 69:
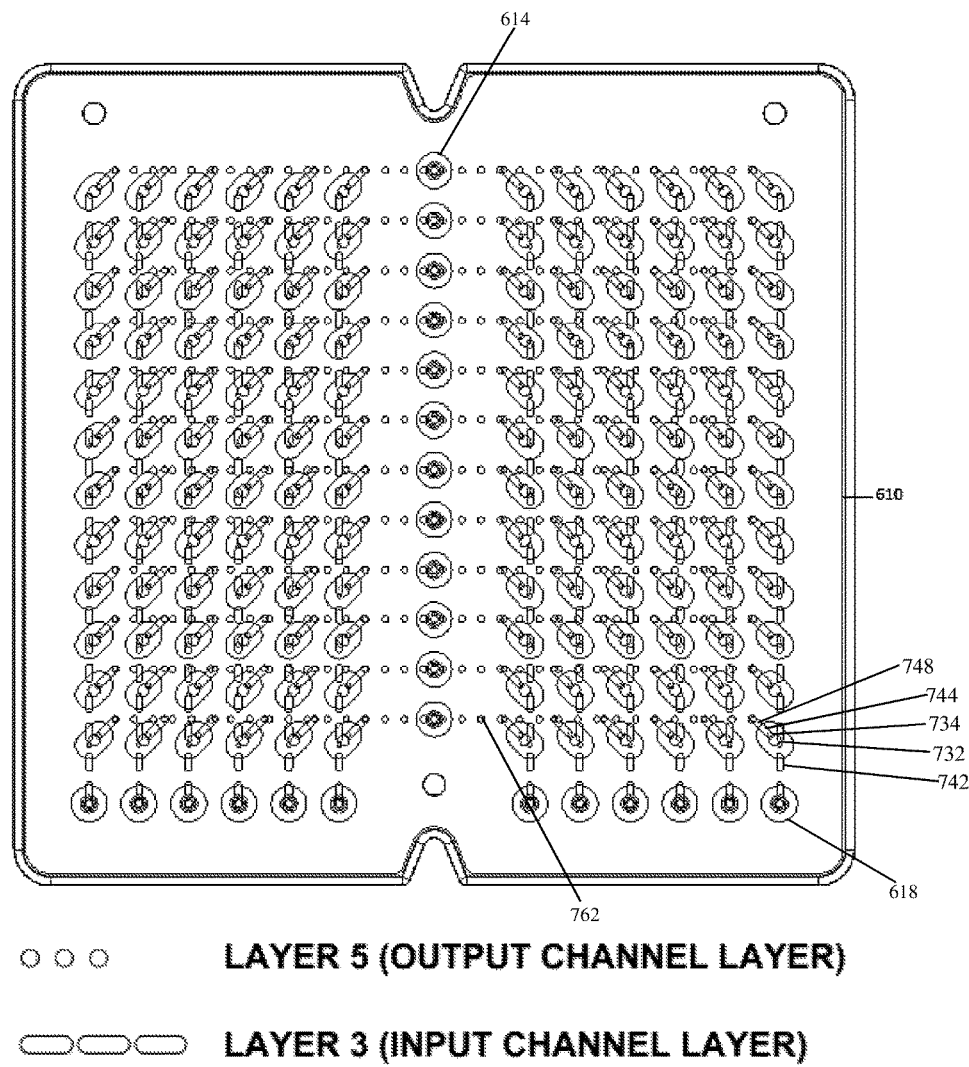
FIG. 69 is a schematic diagram illustrating possible fluid flow paths through a 12×12-fluidic manifold cartridge.

The flow paths through the cartridge 610 is shown schematically in FIG. 69. Fluid enters through fluid and let ports 618. The fluid traverses the layers of the cartridge 610 as previously described until reaching the fluid input flow channel 742. Fluid flows through the fluid input flow channel 742 until a valve is encountered which is open. In this case, the fluid inlet opening 732 will be open for fluid flow due to retraction of the corresponding portions 722 of the membrane layer 720 into the valve seat 712 of the valve layer 710. Fluid will flow to the respective fluid outlet openings 734, and then traverse the fluid valve output channel 744 until reaching a portion which corresponds to a respective fluid output via 752 of the fluid via layer 750. The fluid then traverses to the fluid output channel 722 of the fluid output channel layer 720. Fluid flows through the fluid output channel 722 until reaching the location of the fluid outlet openings 718, whereupon the fluid can exit the fluidic manifold cartridge through the outlet ports 614.

FIG. 69 reveals that each valve is uniquely coordinated with a particular fluid input channel 742 and a particular fluid output channel 722. Accordingly, by suitable operation of the valves using utilizing a processor acting on the control gas fluid flows can be directed in a multitude of different directions and more than one input can be combined in a fluid output by suitable operation of the valves.

This invention can be embodied in other forms without departing from the spirit or essential attributes thereof, and accordingly reference should be made to the following claims to determine the scope of the invention. Although the invention has been described with reference to perifusion, it will be appreciated that the invention can have utility in many other fluid handling operations, such as for example, chemical process operations, drug delivery and fluid transport operations.

I claim:

1. A cartridge for a fluidic manifold system for directing the flow of source fluids, comprising:
    a valve seat layer having a plurality of valve seats, and a plurality of control fluid openings in fluid connection with the valve seats, the valve seats defining a fluid flow path from an inlet location to an outlet location;
    a flexible membrane layer proximal and adjacent to the valve seat layer, and operable under the influence of a control fluid moving through the control fluid openings to flex against the valve seats and to thereby permit fluid flow from the inlet location to the outlet location of the valve seats;
    a fluid input channel layer adjacent to the flexible membrane layer, and on an opposite side of the flexible membrane layer from the valve seat layer, the fluid input channel layer comprising a plurality of elongated slots defining fluid input channels, a portion of the flexible membrane layer forming a wall enclosing on one side the fluid input channels, each elongated input channel intersecting with the inlet locations of valve seats associated with that input channel, the elongated fluid input channels directing fluid to the inlet locations of the associated valve seats, the fluid input channel layer further comprising fluid output openings aligned with the outlet locations of the valve seats;
    a fluid via layer adjacent the fluid input channel layer, a portion of the fluid via layer forming a wall enclosing on one side the elongated input channel slots, the fluid via layer comprising a plurality of fluid output vias in fluid connection with the fluid output openings of the fluid input channel layer, and further comprising a plurality of fluid input vias in fluid communication with the elongated fluid input channels of the fluid input channel layer to permit fluid to flow through the fluid via layer to the fluid input channels;

a fluid output channel layer adjacent to the fluid via layer, and comprising a plurality of slots defining elongated fluid output channels for receiving fluid from the fluid output vias of the fluid via layer, each elongated fluid output channel communicating with a plurality of the fluid output vias of the fluid via layer, a portion of the fluid via layer forming a wall enclosing on one side the fluid output channels, the fluid output channel layer further comprising a plurality of fluid input openings in fluid communication with the fluid input vias of the fluid via layer for permitting the passage of input fluid through the fluid output channel layer; and, a fluid inlet/outlet layer adjacent to the fluid output channel layer, a portion of the fluid input output channel layer forming a wall enclosing on one side the elongated fluid output channels, the fluid inlet/outlet layer comprising a plurality of fluid inlet openings in fluid communication with the fluid input openings of the fluid output channel layer, and further comprising a plurality of fluid outlet openings in fluid communication with the fluid output channels of the fluid output channel layer;

wherein fluid from any fluid input opening can be directed to any fluid output opening.

2. The fluidic manifold cartridge of claim 1, wherein the fluid is a liquid.

3. The fluidic manifold cartridge of claim 1, wherein the control fluid is a gas.

4. The fluidic manifold cartridge of claim 1, wherein the fluidic manifold system is a perifusion system.

* * * * *